United States Patent
Yacoby-Zeevi

(10) Patent No.: US 10,624,839 B2
(45) Date of Patent: Apr. 21, 2020

(54) DOPA DECARBOXYLASE INHIBITOR COMPOSITIONS

(71) Applicant: NeuroDerm, Ltd., Rehovot (IL)

(72) Inventor: Oron Yacoby-Zeevi, Moshav Bitsaron (IL)

(73) Assignee: NeuroDerm, Ltd., Rehovot (IL)

(*) Notice: Subject to any disclaimer, the term of this patent is extended or adjusted under 35 U.S.C. 154(b) by 0 days.

(21) Appl. No.: 16/008,228

(22) Filed: Jun. 14, 2018

(65) Prior Publication Data

US 2019/0151233 A1    May 23, 2019

Related U.S. Application Data

(62) Division of application No. 14/645,848, filed on Mar. 12, 2015, now Pat. No. 10,022,320.

(60) Provisional application No. 61/990,967, filed on May 9, 2014, provisional application No. 61/952,477, filed on Mar. 13, 2014.

(51) Int. Cl.

| | |
|---|---|
| *A61K 9/00* | (2006.01) |
| *A61K 31/133* | (2006.01) |
| *A61K 47/26* | (2006.01) |
| *A61K 47/18* | (2017.01) |
| *A61K 47/22* | (2006.01) |
| *A61K 31/198* | (2006.01) |

(52) U.S. Cl.
CPC .......... *A61K 9/0019* (2013.01); *A61K 31/133* (2013.01); *A61K 31/198* (2013.01); *A61K 47/183* (2013.01); *A61K 47/22* (2013.01); *A61K 47/26* (2013.01); *A61K 9/0014* (2013.01)

(58) Field of Classification Search
CPC ............................ A61K 31/133; A61K 31/198
See application file for complete search history.

(56) References Cited

U.S. PATENT DOCUMENTS

| | | |
|---|---|---|
| 3,769,424 A | 10/1973 | Bayne |
| 3,936,495 A | 2/1976 | Sullivan, Jr. |
| 3,961,060 A | 6/1976 | Fuxe |
| 4,166,452 A | 9/1979 | Generales, Jr. |
| 4,241,082 A | 12/1980 | Baba et al. |

(Continued)

FOREIGN PATENT DOCUMENTS

| | | |
|---|---|---|
| CA | 2143070 A1 | 8/1995 |
| CN | 101022784 A | 8/2007 |

(Continued)

OTHER PUBLICATIONS

"Duodopa Intestinal Gel," Electronic Medicines Compendium, XP-002724129, retrieved from http://www.medicines.org.uk/emc/medicine/20786/SPC/Duodopa+ge;#composition on Sep. 5, 2014. (2013), 7 pages.

(Continued)

*Primary Examiner* — San Ming R Hui
(74) *Attorney, Agent, or Firm* — Goodwin Procter LLP

(57) ABSTRACT

Disclosed herein are formulations containing carbidopa and optionally levodopa, arginine, and other components that have reduced levels of impurities and toxins, particularly degradation productions. Also disclosed herein are methods of treatment diseases or conditions relating to a loss of dopamine or dopaminergic neurons using such formulations, methods of making such formulations, and kits that include such formulations.

10 Claims, 5 Drawing Sheets

(56) References Cited

U.S. PATENT DOCUMENTS

| | | |
|---|---|---|
| 4,256,108 A | 3/1981 | Theeuwes |
| 4,265,874 A | 5/1981 | Bonsen et al. |
| 4,409,233 A | 10/1983 | Tsukada et al. |
| 4,642,316 A | 2/1987 | Fawzi et al. |
| 4,684,666 A | 8/1987 | Haas |
| 4,826,875 A | 5/1989 | Chiesi |
| 4,832,957 A | 5/1989 | Dempski et al. |
| 4,962,223 A | 10/1990 | Cannata et al. |
| 4,963,568 A | 10/1990 | Schoenleber et al. |
| 5,350,769 A | 9/1994 | Kasai et al. |
| 5,861,423 A | 1/1999 | Caldwell et al. |
| 5,877,176 A | 3/1999 | Gross |
| 6,153,615 A | 11/2000 | Gross |
| 6,166,083 A | 12/2000 | Barrett et al. |
| 6,245,917 B1 | 6/2001 | Bosch et al. |
| 6,274,168 B1 | 8/2001 | Addicks et al. |
| 6,348,965 B1 | 2/2002 | Palladino et al. |
| 6,500,867 B1 | 12/2002 | Virkki et al. |
| 6,620,432 B2 | 9/2003 | Addicks et al. |
| 6,716,452 B1 | 4/2004 | Piccariello et al. |
| 6,746,688 B1 | 6/2004 | Kushnir et al. |
| 6,878,529 B2 | 4/2005 | Harrow et al. |
| 6,974,591 B2 | 12/2005 | Kendrup et al. |
| 7,201,923 B1 | 4/2007 | Van Lengerich |
| 7,223,776 B2 | 5/2007 | Surivet et al. |
| 7,309,719 B1 | 12/2007 | Aomatsu |
| 7,479,498 B2 | 1/2009 | Keller |
| 7,560,100 B2 | 7/2009 | Pinchasi et al. |
| 7,589,233 B2 | 9/2009 | Chandran |
| 7,709,494 B2 | 5/2010 | Defossa et al. |
| 7,863,336 B2 | 1/2011 | Yacoby-Zeevi et al. |
| 8,048,926 B2 | 11/2011 | Atlas |
| 8,058,243 B2 | 11/2011 | Tyers et al. |
| 8,173,840 B2 | 5/2012 | Chandran |
| 8,193,243 B2 | 6/2012 | Yacoby-Zeevi et al. |
| 8,263,125 B2 | 9/2012 | Vaya et al. |
| 8,273,731 B2 | 9/2012 | Heldman |
| 8,921,356 B2 | 12/2014 | Heldman |
| 9,040,577 B2 | 5/2015 | Yacoby-Zeevi et al. |
| 9,040,578 B2 | 5/2015 | Yacoby-Zeevi et al. |
| 9,040,589 B2 | 5/2015 | Yacoby-Zeevi et al. |
| 9,040,590 B2 | 5/2015 | Yacoby-Zeevi et al. |
| 9,101,663 B2 | 8/2015 | Yacoby-Zeevi et al. |
| 9,381,249 B2 | 7/2016 | Yacoby-Zeevi et al. |
| 9,415,108 B2 | 8/2016 | Yacoby-Zeevi et al. |
| 9,421,267 B2 | 8/2016 | Yacoby-Zeevi et al. |
| 9,993,451 B2 | 6/2018 | Yacoby-Zeevi et al. |
| 10,022,320 B2 | 7/2018 | Yacoby-Zeevi |
| 10,258,585 B2 | 4/2019 | Yacoby-Zeevi |
| 2001/0043945 A1 | 11/2001 | Addicks et al. |
| 2002/0028799 A1 | 3/2002 | Naylor et al. |
| 2002/0099013 A1 | 7/2002 | Piccariello et al. |
| 2002/0102707 A1 | 8/2002 | Harrow et al. |
| 2003/0119714 A1 | 6/2003 | Naylor et al. |
| 2003/0152628 A1 | 8/2003 | Licht et al. |
| 2004/0039033 A1 | 2/2004 | Atwal et al. |
| 2005/0038023 A1 | 2/2005 | Bebbington et al. |
| 2005/0053669 A1 | 3/2005 | Friedl et al. |
| 2005/0070608 A1* | 3/2005 | Remenar ............ A61K 9/0095 514/567 |
| 2005/0163850 A1 | 7/2005 | Wong et al. |
| 2005/0163859 A1 | 7/2005 | Murthy et al. |
| 2005/0233945 A1 | 10/2005 | Brown et al. |
| 2006/0025385 A1 | 2/2006 | Atlas |
| 2006/0041014 A1 | 2/2006 | Naylor et al. |
| 2006/0088607 A1 | 4/2006 | Stefano et al. |
| 2006/0159751 A1 | 7/2006 | Gogia et al. |
| 2006/0241183 A1 | 10/2006 | Karoum |
| 2007/0191428 A1 | 8/2007 | Rao et al. |
| 2008/0051459 A1 | 2/2008 | Nyholm et al. |
| 2008/0139655 A1 | 6/2008 | Bortz et al. |
| 2008/0187590 A1 | 8/2008 | Vahervuo |
| 2008/0255235 A1 | 10/2008 | Segrell |
| 2010/0298428 A1 | 11/2010 | Yacoby-Zeevi et al. |
| 2010/0298429 A1 | 11/2010 | Yacoby-Zeevi et al. |
| 2011/0269833 A1 | 11/2011 | Yacoby-Zeevi et al. |
| 2011/0294889 A1 | 12/2011 | Segrell |
| 2012/0115823 A1 | 5/2012 | Price et al. |
| 2013/0116215 A1 | 5/2013 | Coma et al. |
| 2013/0123485 A1 | 5/2013 | Park et al. |
| 2013/0253056 A1 | 9/2013 | Nemas et al. |
| 2013/0338143 A1 | 12/2013 | Yacoby-Zeevi et al. |
| 2014/0051755 A1 | 2/2014 | Yacoby-Zeevi et al. |
| 2014/0088192 A1 | 3/2014 | Heller et al. |
| 2014/0249228 A1 | 9/2014 | Yacoby-Zeevi et al. |
| 2014/0249229 A1 | 9/2014 | Yacoby-Zeevi et al. |
| 2014/0249230 A1 | 9/2014 | Yacoby-Zeevi et al. |
| 2014/0249231 A1 | 9/2014 | Yacoby-Zeevi et al. |
| 2015/0217046 A1 | 8/2015 | Heller et al. |
| 2015/0352212 A1 | 12/2015 | Yacoby-Zeevi et al. |
| 2016/0022573 A1 | 1/2016 | Yacoby-Zeevi et al. |
| 2016/0106765 A1 | 4/2016 | Cardinal-David et al. |
| 2016/0151317 A1 | 6/2016 | Yacoby-Zeevi et al. |
| 2017/0157077 A1 | 6/2017 | Yacoby-Zeevi et al. |
| 2017/0157079 A1 | 6/2017 | Yacoby-Zeevi |
| 2017/0196828 A1 | 7/2017 | Yacoby-Zeevi et al. |
| 2017/0296491 A1 | 10/2017 | Yacoby-Zeevi et al. |
| 2019/0125708 A1 | 5/2019 | Yacoby-Zeevi et al. |

FOREIGN PATENT DOCUMENTS

| Country | Number | Date | Notes |
|---|---|---|---|
| CN | 101669925 A | 3/2010 | |
| DE | 2838232 A1 | 3/1979 | |
| EP | 1077692 A1 | 2/2001 | |
| EP | 1462101 A1 | 9/2004 | |
| EP | 2656856 A2 | 10/2013 | |
| IN | 244675 B | 12/2010 | |
| IN | 251149 B | 2/2012 | |
| JP | 54-50700 A | 4/1979 | |
| JP | S56115749 | 9/1981 | |
| WO | WO-1984/01501 A1 | 4/1984 | |
| WO | WO-1996/037226 A2 | 11/1996 | |
| WO | WO-1998/016208 A1 | 4/1998 | |
| WO | WO-2000/054773 A1 | 9/2000 | |
| WO | WO-2001/001984 A1 | 1/2001 | |
| WO | WO-2004069146 A2 | 8/2004 | |
| WO | WO-2005/099678 A1 | 10/2005 | |
| WO | WO-2006/006929 A1 | 1/2006 | |
| WO | WO-2007/138086 A1 | 12/2007 | |
| WO | WO-2008/124330 A2 | 10/2008 | |
| WO | WO-2010/055133 A1 | 5/2010 | |
| WO | WO-2010/134074 A1 | 11/2010 | |
| WO | WO-2010134074 A1 * | 11/2010 | ........... A61K 9/0019 |
| WO | WO-2012/006959 A1 | 1/2012 | |
| WO | WO-2012/066538 A1 | 5/2012 | |
| WO | WO-2014/141261 A1 | 9/2014 | |
| WO | WO-2015/136538 A1 | 9/2015 | |
| WO | WO-2017/090039 A2 | 6/2017 | |
| WO | WO-2018/154447 A1 | 8/2018 | |
| WO | WO-2019/038637 A1 | 2/2019 | |
| WO | WO-2019/038638 A1 | 2/2019 | |
| WO | WO-2019/038639 A1 | 2/2019 | |

OTHER PUBLICATIONS

National Institutes of Health (2010) 'Pharmacokinetics of Levodopa/Carbidopa Infusion With and Without Oral Catechol-O-Methyl Transferase (COMT) Inhibitors (DuoCOMT),' U.S. National Library of Medicine, ClinicalTrials.gov, ClinicalTrials.gov Identifier: NCT00906828, XP-002724128, retrieved from URL://http://clinicaltrials.gov/ct2/show/NCT00906828 on Sep. 5, 2014 (3 pages).

Ahtila S et al., (1995) 'Effect of Entacapone, a COMT Inhibitor, on the Pharmacokinetics and metabolism of Levodopa After Administration of Controlled-Release Levodopa-Carbidopa in Volunteers,' Clin Neuropharmacol, 18(1):46-57.

Anonymous, (2002), "Levodopa: Management of Parkinson's Disease," Mov Disord, 17(Suppl 4); S23-S37.

Atlas D, (2016), "DopAmide: Novel, Water-Soluble, Slow-Release l-dihydroxyphenylalanine (l-DOPA) Precursor Moderates l-DOPA Conversion to Dopamine and Generates a Sustained Level of Dopamine at Dopaminergic Neurons," CNS Neurosci Ther, 22(6):461-7.

(56) References Cited

OTHER PUBLICATIONS

Chun Ik et al., (2011), "Design and Evaluation of Levodopa Methyl Ester Intranasal Delivery Systems," J Parkinsons Dis, 1 (1):101-7.
Di Stefano A et al., (2009), "New Drug Delivery Strategies for Improved Parkinson's Disease Therapy," Expert Opin Drug Deliv, 6(4):389-404.
Diederich C et al., (1997), 'Effects of L-DOPA/Carbidopa Administration on the Levels of L-DOPA, Other Amino Acids and Related Compounds in the Plasma, Brain and Heart of the Rat,' Pharmacology, 55(3):109-16.
Food and Drug Administration (2008) "NDA 17-555/S-069: Sinemet (Carbidopa-Levodopa) Tablets," [online] Retrieved from the internet on Jun. 20, 2018, at: http://www.accessdata.fda.gov/drugsatfda_docs/label/2008/017555s069lbl.pdf (13 pages).
Gordon, M., et al., (2007) "Intravenous Levodopa Administration in Humans Based on a Two-Compartment Kinetic Model," *J. Neuroscience Methods*, 159: 300-307.
Hirano, et al., (2008) "Arginine Increases the Solubility of Coumarin: Comparison with Salting-in and Salting-out Additives," *J. Biochem*, 144 (3): 363-369.
Ingman, K et al., (2012) 'The Effect of Different Dosing Regimens of Levodopa/Carbidopa/Entacapone on Plasma Levodopa Concentrations,' Eur J Clin Pharmacol, 68:281-289.
International Search Report for International Application No. PCT/IB2018/051048, dated May 21, 2018 (3 pages).
International Search Report for International Application No. PCT/IL04/00103, dated Aug. 7, 2006 (3 pages).
International Search Report for PCT/IL2010/000400, dated Jul. 29, 2010, 4 pages.
International Search Report for PCT/IL2011/000881, dated Apr. 3, 2012, 5 pages.
International Search Report for PCT/IL2014/050261,dated May 30, 2014, 4 pages.
International Search Report for PCT/IL2015/050258, dated Aug. 13, 2015 (3 pages).
International Search Report for PCT/IL2016/051261, dated May 29, 2017 (6 pages).
Jog et al. (2008) 'Naturalistic Evaluation of Entacapone in Patients with Signs and Symptons of L-Dopa Wearing-Off,' Current Medical Research and Opinions, 24:11, 3207-3215.
Kharkevich, D.A., (1996) "Pharmacology M., Medicine." 1 page. (Abstract only).
Kurth, MC (1997) 'Using Liquid Levodopa in the Treatment of Parkinson's Disease. A Practical Guide,' Drugs & Aging, 10 (5): 332-340.
López Lozano, JJ et al., (1995) 'Preparation of a Levodopa/Carbidopa Solution in Ascorbic Acid (Citridopa) and Chromatographic and Electrochemical Assessment of its Stability over 24 Hours,' Neurologia 10:155-158 (Abstract only).
MacEwen, et al., (1981) "Chronic Inhalation Toxicity of Hydrazine: Oncogenic Effects," Air Force Aerospace Medical Research Laboratory, pp. 1-67.
Martinez, et al.,(1999) "Hypothesis: Can N-Acetylcysteine Be Beneficial in Parkinson's Disease?", Life Sciences, 64(15):1253-1257.
Mashkovsky, M.D., (2012) "Pharmaceuticals" 16th Edition. Moscow, New wave. 1 page. (Abstract only).
Mehlisch, et al., (2002) "A Controlled Comparative Study of Ibuprofen Arginate Versus Conventional Ibuprofen in the Treatment of Postoperative Dental Pain," *J. Clin. Pharmacol*., 42: 904-911.
Nahata, et al.,(2000) "Development of Two Stable Oral Suspensions of Levodopa-Carbidopa for Children with Amblyopia," *J. Pediatric Ophthal. & Strab*., 37:333-337.
Nord, M. et al., (2010) "The Effect of Peripheral Enzyme Inhibitors on Levodopa Concentrations in Blood and CSF," *Movement Disorders*, 25(3): 363-367.
Nutt JG, (2008), 'Pharmacokinetics and Pharmacodynamics of Levodopa,' *Mov. Disord*., S580-4.
Nutt, et al., (1997) "Motor Fluctuations During Continuous Levodopa Infusions in Patients with Parkinson's Disease," *Movement Disorders*, 12(3):285-292.
Nyholm, D. (2006) "Enteral Levodopa/Carbidopa Gel Infusion for the Treatment of Motor Fluctuations and Dyskinesias in Advanced Parkinson's Disease," *Expert Review of Neurotherapeutics*, 6(10): 1403-1411.
Nyholm, D., et al., (2012) "Levodopa Infusion Combined with Entacapone or Tolcapone in Parkinson Disease: a Pilot Trial," *European Journal of Neurology*, 19: 820-826.
Office action dated Dec. 27, 2017, issued in connection with Russian Patent Application No. 2015143112 (13 pages).
Office Action dated Sep. 12, 2018, issued in connection with Russian Patent Application No. 2016135952 (12 pages).
Olanow, C.W. (2008) "Levopoda/Dopamine Replacement Strategies in Parkinson's Disease—Future Directions," *Movement Disorders*, 23:S613-S622.
Pappert, et al., (1997) "Clinical/Scientific Notes—The Stability of Carbidopa in Solution," Movement Disorders, vol. 12, pp. 608-623.
Pardo, et al., (1993) "Ascorbic acid protects against levodopa-induced neurotoxicity on a catecholamine-rich human neuroblastoma cell line", *Mov. Disord*., 8(3):278-284. (Abstract Only).
Redenti, et al., (2001) "Cyclodextrin Complexes of Salts of Acidic Drugs. Thermodynamic Properties, Structural Features, and Pharmaceutical Applications," *Journal of Pharmaceutical Sciences*, 90(8): 979-986.
Roche Products (New Zealand) Limited. (2015) "Madopar Consumer Medicine Information." 1-9.
Steiger, M., et al., (1991) "The Clinical Efficacy of Oral Levodopa Methyl Ester Solution in Reversing Afternoon "Off" Periods in Parkinson's Disease," Clin. Neuropharmacol., 14:241-244.
Stocchi et al., (2005), "Intermittent vs Continuous Levodopa Administration in Patients With Advanced Parkinson Disease," Arch Neurol, vol. 62, pp. 905-910.
Tsumoto, K., et al., (2004) "Role of Arginine in Protein Refolding, Solubilization, and Purification," *Biotechnol. Prog*., 20:1301-1308.
Umezawa H., et al., (1975) "Isolation of Isoflavones Inhibiting Dopa Decarboxylase From Fungi and Streptomyces," J Antibiot, 28(12):947-52.
Written Opinion for International Application No. PCT/IL2015/050258, dated Aug. 13, 2015 (6 pages).
Written Opinion of the International Search Authority for PCT/IL2010/000400 dated Jul. 29, 2010, 8 pages.
Written Opinion of the International Search Authority for PCT/IL2011/000881 dated Apr. 3, 2012, 6 pages.
Written Opinion of the International Search Authority for PCT/IL2014/050261 dated May 30, 2014, 5 pages.
Written Opinion of the International Searching Authority for International Application No. PCT/IB2018/051048, dated May 21, 2018 (7 pages).
Written Opinion of the International Searching Authority for International Application No. PCT/IL04/00103, dated Aug. 7, 2006 (4 pages).
Written Opinion of the International Searching Authority for PCT/IL2016/051261, dated May 29, 2017 (14 pages).
Yacoby-Zeevi, O., et al. (2010) "Markedly Enhanced Levodopa Pharmacokinetics from Continuous Subcutaneous Carbidopa Administration," European Journal of Neurology, 17 (Suppl. 3): 52.
U.S. Appl. No. 12/781,357, Continuous Administration of Dopa Decarboxylase Inhibitors and Composition for Same, filed May 17, 2010, Issued, U.S. Pat. No. 8,193,243, issued on Jun. 5, 2012.
U.S. Appl. No. 12/836,130, Continuous Administration of Dopa Decarboxylase Inhibitors and Composition for Same, filed Jul. 14, 2010, Issued, U.S. Pat. No. 7,863,336, issued on Jan. 4, 2011.
U.S. Appl. No. 12/961,534, Continuous Administration of Dopa Decarboxylase Inhibitors and Composition for Same, filed Dec. 7, 2010, Issued, U.S. Pat. No. 9,101,663, issued on Aug. 11, 2015.
U.S. Appl. No. 14/276,211, Continuous Administration of Dopa Decarboxylase Inhibitors and Composition for Same, filed May 13, 2014, Issued, U.S. Pat. No. 9,040,589, issued on May 26, 2015.
U.S. Appl. No. 14/276,235, Continuous Administration of Dopa Decarboxylase Inhibitors and Composition for Same, filed May 13, 2014, Issued, U.S. Pat. No. 9,040,590, issued on May 26, 2015.

(56) References Cited

OTHER PUBLICATIONS

U.S. Appl. No. 14/789,214, Continuous Administration of Dopa Decarboxylase Inhibitors and Compositions for Same, filed Jul. 1, 2015, Issued, U.S. Pat. No. 9,993,451, issued on Jun. 12, 2018.
U.S. Appl. No. 15/992,979 Continuous Administration of Dopa Decarboxylase Inhibitors and Compositions for Same, filed May 30, 2018, Pending.
U.S. Appl. No. 13/796,232, Continuous Administration of Levodopa and/or Dopa Decarboxylase Inhibitors and Compositions for Same, filed Mar. 12, 2013, Abandoned, Publication No. 2013-0253056, published on Sep. 26, 2013.
U.S. Appl. No. 15/244,326, Continuous Administration of Levodopa and/or Dopa Decarboxylase Inhibitors and Compositions for Same, filed Aug. 23, 2016, Published, U.S. Publication No. 2017-0196828, published on Jul. 13, 2017.
U.S. Appl. No. 13/885,518 Continuous Administration of L-Dopa, Dopa Decarboxylase Inhibitors, Catechol-O-Methyl Transferase Inhibitors and Compositions for Same, filed Oct. 29, 2013, Issued U.S. Pat. No. 9,421,267, issued on Aug. 23, 2016.
U.S. Appl. No. 14/243,625 Continuous Administration of L-Dopa, Dopa Decarboxylase Inhibitors, Catechol-O-Methyl Transferase Inhibitors and Compositions for Same, filed Apr. 2, 2014, Issued, U.S. Pat. No. 9,040,577, issued on May 26, 2015.
U.S. Appl. No. 14/243,638 Continuous Administration of L-Dopa, Dopa Decarboxylase Inhibitors, Catechol-O-Methyl Transferase Inhibitors and Compositions for Same, filed Apr. 2, 2014, Issued, U.S. Pat. No. 9,040,578, issued on May 26, 2015.
U.S. Appl. No. 15/209,423, Continuous Administration of L-Dopa, Dopa Decarboxylase Inhibitors, Catechol-O-Methyl Transferase Inhibitors and Compositions for Same, filed Jul. 13, 2016, Published, U.S. Publication No. 2017-0157077, published on Jun. 8, 2017.
U.S. Appl. No. 14/774,938 Method for Treatment of Parkinson's Disease, filed Sep. 11, 2015, Published, U.S. Publication No. 20160022573, published on Jan. 28, 2016.
U.S. Appl. No. 14/645,848, Dopa Decarboxylase Inhibitor Compositions, filed Mar. 12, 2015, Issued, U.S. Pat. No. 10,022,320, issued on Jul. 17, 2018.
U.S. Appl. No. 15/438,472, Dopa Decarboxylase Inhibitor Compositions, filed Feb. 21, 2017, Allowed, U.S. Publication No. 20170157079, published on Jun. 8, 2017.
U.S. Appl. No. 16/353,544, Dopa Decarboxylase Inhibitor Compositions, filed Mar. 14, 2019, Pending.
U.S. Appl. No. 15/360,165, Pharmaceutical Compositions Comprising Levodopa Amide and Uses Thereof, filed Nov. 23, 2016, Published, U.S. Publication No. 2017-0296491, published on Oct. 19, 2017.
U.S. Appl. No. 11/196,739, L-Dopa Amide Derivatives and Uses Thereof, filed Aug. 4, 2005, Issued, U.S. Pat. No. 8,048,926, issued on Nov. 1, 2011.
"Dihydroxphenylalanine" PubmChem CID No. 6971033, (retrieved on Jul. 8, 2019, from the Internet at <<https://pubchem.ncbi.nlm.nih.gov/compound/6971033>>)(24 pages).
"Levodopa," in *Encyclopedia of Drugs*, p. 471 (Moscow, RLS, 2001)(2 pages; English language translation of Office Action).
Aldea G, et al., (2004) Abstract 15, entitled "Comparison of the speed of absorption of S(+)- ibuprofen in two pharmaceutical specialties: ibuprofen (arginate) and dexibuprofen" in *Abstract Pamphlet for the XIX Congress of the Spanish Society of Clinical Pharmacology*, XIX Congress of the Spanish Society of Clinical Pharmacology, Oct. 28-30, 2004, Santander, Spain (56 pages).
Banerjee, RC, (1979) "Aminonitriles and Aminothioamides Related to Natural Amino Acids," *International Journal of Peptide and Protein Res.* 14(3):234-46.
Elder D., et al., (2013) "Use of Pharmaceutical Salts and Cocrystals to Address the Issue of Poor Solubility," *International Journal of Pharmaceutics*, 453(1):88-100.
English language translation of Official Action issued in connection with Russian Patent Application No. 2011149976/15, dated Sep. 15, 2014 (6 pages).

Hilfiker et al., "Relevance of Solid-state Properties for Pharmaceutical Products" in *Polymorphism: in the Pharmaceutical Industry*, p. 1-19 (Ed. Hilfiker, WILEY-VCH Verlag GmbH & Co. KGaA, Weinheim, 2006).
International Search Report for International Application No. PCT/162018/056125, dated Jan. 14, 2019 (5 pages).
International Search Report for International Application No. PCT/162018/056126, dated Nov. 26, 2018 (4 pages).
International Search Report for International Application No. PCT/162018/056127, dated Nov. 26, 2018 (4 pages).
Levin, O.S. (2008) "Diagnosis and treatment of restless legs syndrome" *Attending Physician*5(8) (retrieved Jul. 8, 2019, from the internet at <<https://www.Ivrach.ru/2008/05/5154263/>>) (10 pages).
Paulekuhn, GS, et al. (2007) "Trends in Active Pharmaceutical Ingredient Salt Selection based on Analysis of the Orange Book Database," *Journal of Medicinal Chemistry, American Chemical Society*, 50(26):6665-6672.
CAPLUS Registry No. 120346-34-1 (1989), retrieved from CAPLUS on May 16, 2008 (2 pages).
CAPLUS Registry No. 34996-80-0 (1984), retrieved from CAPLUS on May 16, 2008 (1 page).
CAPLUS Registry No. 73148-96-6 (1984), retrieved from CAPLUS database on May 16, 2008 (1 page).
Technology of Dosage Forms, in *Medicine*, vol. 1, §10.3, p. 187-91, and §14.2, p. 223-4 (Ed. T.S. Kondrat'eva, Moscow, 1991)(7 pages; English language translation of Office Action).
Written Opinion of the International Searching Authority for International Application No. PCT/162018/056125, dated Jan. 14, 2019 (10 pages).
Written Opinion of the International Searching Authority for International Application No. PCT/162018/056126, dated Nov. 26, 2018 (10 pages).
Written Opinion of the International Searching Authority for International Application No. PCT/162018/056127, dated Nov. 26, 2018 (7 pages).
Zhou, et al. (2010) "Design, Synthesis and Biological Evaluation of L-dopa Amide Derivatives as Potential Prodrugs for the Treatment of Parkinson's Disease," *European Journal of Medical Chemistry*, 45(9):4035-4042.
"Mutschler Arzneimittelwirkungen" p. 322-325 (Ernst Mutschler et al. eds., Wissenschaftliche Verlagsgesellschaft mbH, 2008)(Cited in Decision rejecting the opposition of European Patent No. 2 432 454, dated Aug. 26, 2019)(6 pages).
"Mutschler Arzneimittelwirkungen: Lehrbuch der Pharmakologie and Toxikologie" p. 327 (Ernst Mutschler et al. eds., Wissenschaftliche Verlagsgesellschaft mbH, 2008)(Cited in Decision rejecting the opposition of European Patent No. 2 432 454, dated Aug. 26, 2019)(3 pages).
"New Zealand standardised formulation batch sheet, Carbidopa/Levodopa (Sinemet®) suspension" (2010) Last updated Dec. 2010 (1 page).
"The Merck Index: an Encyclopedia of Chemicals, Drugs, and Biologicals" p. xv and 784-5 (M. Windholz et al. eds., Merck & Co., Inc., 10th edition, 1983)(4 pages).
AbbVie Ltd (2017) "Duodopa intestinal gel, Summary of Product Characteristics" Updated Dec. 5, 2017 (12 pages).
Appendices II and III, submitted to the European Patent Office on Mar. 16, 2016 in connection with European Application No. EP10725880.8, and cited in the Decision rejecting the opposition of European Patent No. 2 432 454, dated Aug. 26, 2019 (3 pages).
European Patent Office, Opposition Division "Decision rejecting the opposition of European Patent No. 2 432 454" dated Aug. 26, 2019 (13 pages).
J E. Ahlskog "Parkinson's Disease Treatment Guide for Physicians" p. 179-81 (Oxford University Press, 2009) (6 pages).
Kurth et al., (1993) "Oral levodopa/carbidopa solution versus tablets in Parkinson's patients with severe fluctuations: A pilot study," *Neurology*43:1036-9.
L. Braiman-Wiksman (2018) "Experimental Report, A. Stability Testing" p. 1-7.
Merck Sharp & Dohme Limited (2019) "Sinemet 12.5mg/50mg Tablets, Summary of Product Characteristics" Updated Feb. 1, 2019 (7 pages).

(56) References Cited

OTHER PUBLICATIONS

Nagayama, et al. (2004) "The Effect of Ascorbic Acid on the Pharmacokinetics of Levodopa in Elderly Patients with Parkinson Disease," *Clin Neuropharmacol*, 27(6):270-3.

Nationwide Children's Hospital (2010) "Levodopa/Carbidopa Oral Suspension 5mg-1.25mg/mL" (1 page).

Pharminfotech (2011) "Formulation in Pharmacy Practice—eMixt: Levodopa/Carbidopa" Updated Sep. 2011 (retrieved from <http://www.pharminfotech.co.nz/maual/Formulation/mixtures/levodopa/htm> on Apr. 8, 2019)(1 page).

Roche Products Limited (2015) "Package leaflet: Information for the patient" Updated Mar. 2015 (6 pages).

Roche Products Limited (2016) "Madopar 100 mg/25 mg Dispersible Tablets, Summary of Product Characteristics" Updated Mar. 17, 2016 (9 pages).

Roche Products Limited (2016) "Madopar 50 mg/12.5 mg Dispersible Tablets, Summary of Product Characteristics" Updated Mar. 17, 2016 (9 pages).

S. Mondal "Basic Undergraduate Pharmacology" p. 280 (Academic Publishers, Mar. 2010) (3 pages).

U. Moser "Arzneibuch-Kommentar" p. C18 (Wissenschaftliche Verlagsgesellschaft mbH, 1993)(Cited in Decision rejecting the opposition of European Patent No. 2 432 454, dated Aug. 26, 2019)(2 pages).

\* cited by examiner

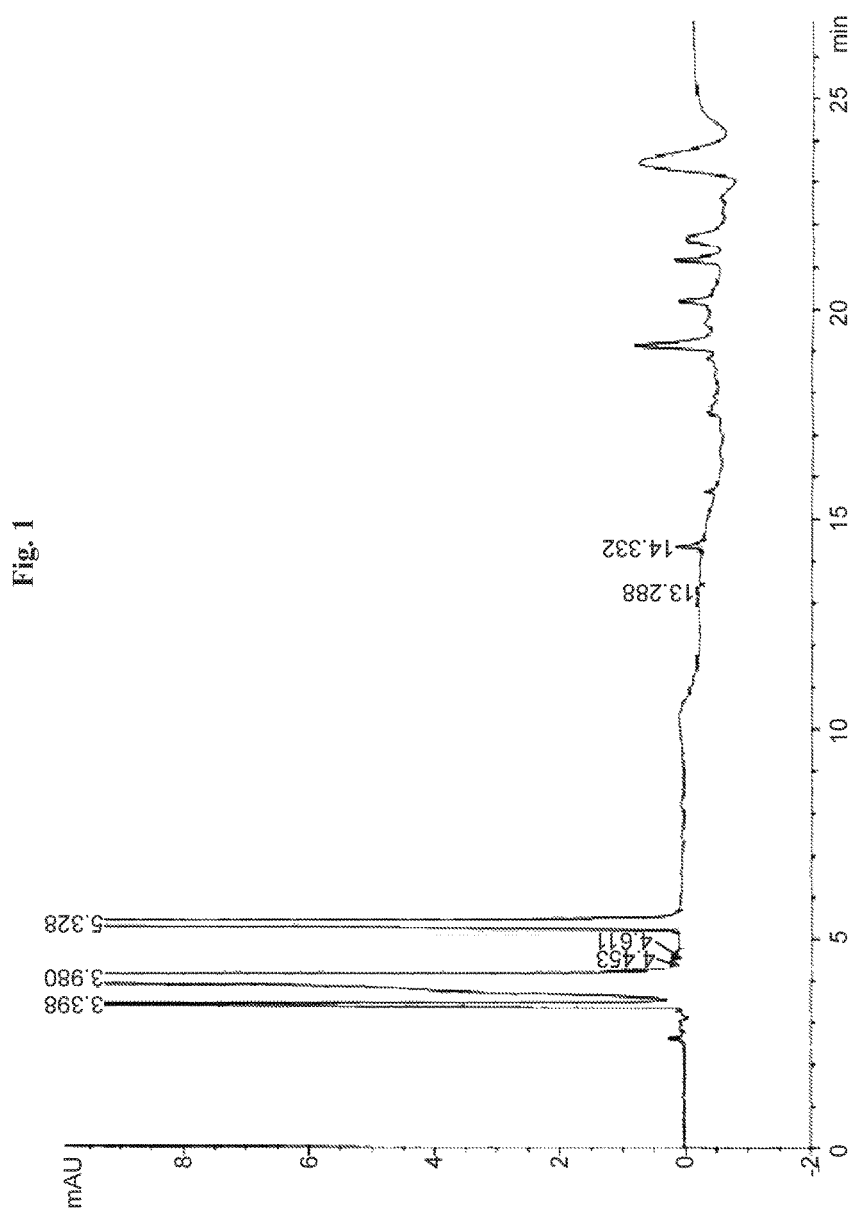

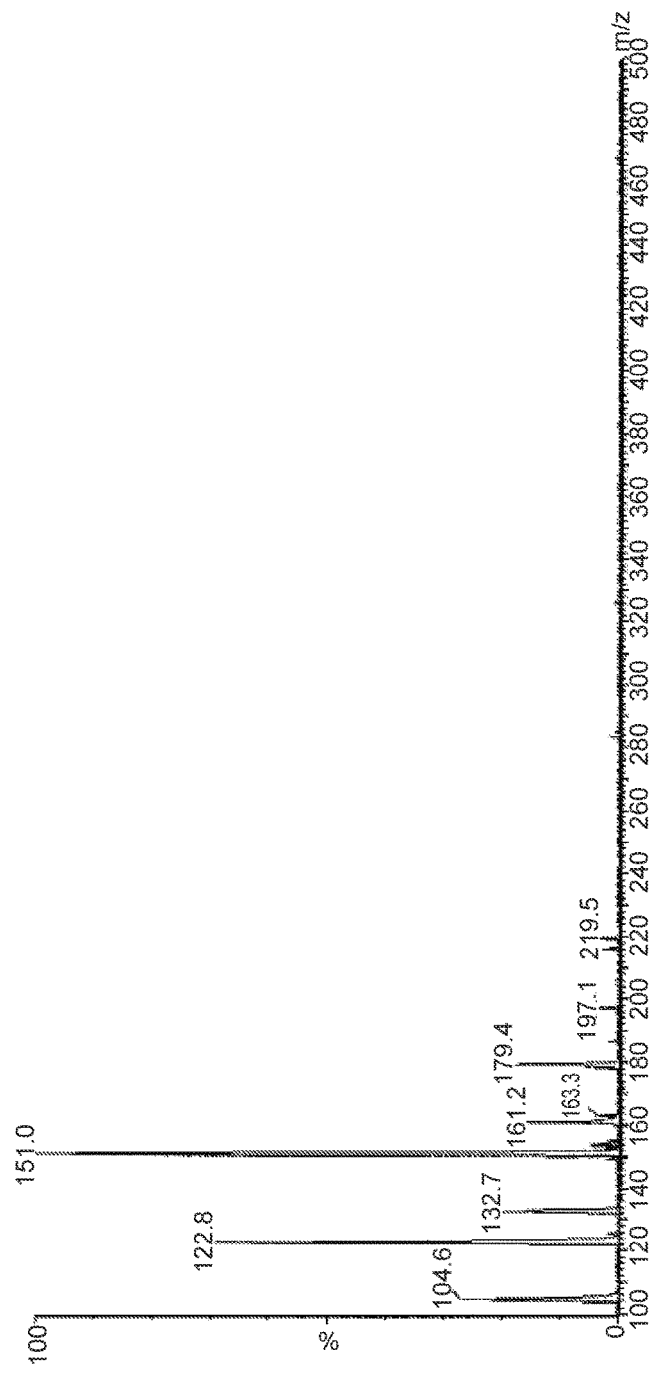

DOPA DECARBOXYLASE INHIBITOR COMPOSITIONS

CROSS-REFERENCE TO RELATED APPLICATIONS

This application is a divisional of U.S. patent application Ser. No. 14/645,848, filed Mar. 12, 2015, which claims the benefit of U.S. Provisional Patent Application No. 61/952,477, filed Mar. 13, 2014, and U.S. Provisional Patent Application No. 61/990,967, filed May 9, 2014, the entire contents of each of which is hereby incorporated by reference for all purposes.

BACKGROUND

Parkinson's disease is a degenerative condition characterized by reduced concentration of the neurotransmitter dopamine in the brain. Levodopa (L-dopa or L-3,4-dihydroxyphenylalanine) is an immediate metabolic precursor of dopamine that, unlike dopamine, is able to cross the blood-brain barrier and is most commonly used for restoring the dopamine concentration in the brain. For the past 40 years, levodopa has remained the most effective therapy for the treatment of Parkinson's disease.

However, levodopa has a short half-life in plasma that, even under best common current standard of care, results in pulsatile dopaminergic stimulation. Long-term therapy is therefore complicated by motor fluctuations and dyskinesia that can represent a source of significant disability for some patients. A therapeutic strategy that could ultimately deliver levodopa/dopamine to the brain in a more continuous and physiologic manner would provide the benefits of standard levodopa with reduced motor complications and is much needed by patients suffering from Parkinson's disease and other neurological or movement disorders (Olanow C W; Mov. Dis. 2008, 23(Suppl. 3):S613-S622). Sustained-release oral levodopa formulations have been developed, but, at best, such preparations have been found to be no more efficacious than standard tablets. Continuous administration of levodopa by intraduodenal administration or infusion has also been attempted by using ambulatory pumps or patches. Such treatments, especially intraduodenal, are extremely invasive and inconvenient.

The metabolic transformation of levodopa to dopamine is catalyzed by the aromatic L-amino acid decarboxylase enzyme, a ubiquitous enzyme with particularly high concentrations in the intestinal mucosa, liver, brain, and brain capillaries. Due to the possibility of extracerebral metabolism of levodopa, it is necessary to administer large doses of levodopa leading to high extracerebral concentrations of dopamine that cause nausea in some patients. Therefore, levodopa is usually administered concurrently with oral administration of a dopa decarboxylase inhibitor, such as carbidopa or benserazide, which reduces by 60-80% the levodopa dose required for a clinical response, and thus prevents certain of its side effects by inhibiting the conversion of levodopa to dopamine outside the brain.

Various oral formulations together with inhibitors of enzymes associated with the metabolic degradation of levodopa are well known, for example, decarboxylase inhibitors such as carbidopa and benserazide, monoamone oxidase (MAO)-A or MAO-B inhibitors such as moclobemide, rasagiline, selegiline, and safinamide, and catechol-O-methyl transferase (COMT) inhibitors such as tolcapone and entacapone. Currently available oral drugs include SINEMET® and SINEMET®CR sustained-release tablets that include carbidopa or levodopa; MADOPAR® tablets containing levodopa and benserazide; and STALEVO® tablets containing carbidopa, entacapone, and levodopa.

Carbidopa is a non-competitive inhibitor of DOPA decarboxylase. When mixed with levodopa, carbidopa inhibits the peripheral conversion of levodopa to dopamine. This results in increased levodopa available for transport to the CNS. Carbidopa also inhibits the metabolism of levodopa in the GI tract, thus, increasing levodopa bioavailability. It is used in Parkinson's disease to reduce the peripheral effect of dopamine. The loss of the hydrazine functional group represents the major metabolic pathway for carbidopa.

Hydrazine ($N_2H_4$), or its salts, are used in the production of pharmaceutical products. It has been the cause of severe adverse effects on the central nervous system, liver, and kidneys. In addition to these effects, experimental animals have also shown the following symptoms: loss of body weight, anemia, hypoglycemia, fatty degeneration of the liver, and convulsions. Hydrazine has also been shown to cause DNA damage, gene mutations, and chromosome aberrations (Environmental health criteria No. 68 hydrazine (1987)) and has induced tumor growth in mice, hamsters, and rats after oral, intraperitoneal, and inhalation administration (MacEwan J D, Vernot E H, Haun C C, et al. (1981)). Hydrazine and its salts are used in the pharmaceutical industry as an intermediate to produce drugs with different therapeutic effects including decarboxylase inhibitors, antihypertensives, and antibacterials. Since hydrazine is toxic and thought to be a possible human carcinogen, its presence is limited in some of these drug substances in the monographs of the European Pharmacopoeia (Ph. Eur.).

Accordingly, there is an ongoing and urgent need for liquid formulations and compositions that can achieve continuous dopaminergic stimulation to treat movement disorders such as Parkinson's disease more effectively containing a safe and tolerable amount of hydrazine.

SUMMARY

This disclosure is directed in part to carbidopa or carbidopa ester formulations (CD), which can include levodopa (e.g., includes levodopa (or a levodopa ester) and carbidopa). In certain embodiments, disclosed carbidopa or carbidopa/levodopa formulations also include two or more antioxidants, e.g., (a) ascorbic acid or a salt thereof (e.g., sodium ascorbate) and (b) another antioxidant, such as cysteine or a cysteine derivative (for example, L-cysteine or N-acetylcysteine (NAC), glutathione, or diacetylcystine), or a sulfite (e.g., sodium sulfite). In particular, we have discovered that CD formulations that include two antioxidants are more stable than those containing just a single antioxidant. Certain disclosed compositions or formulations have improved resistance to degradation (e.g., have minimal amounts of a degradation species, e.g., hydrazine), and/or are significantly stable.

Accordingly, in a first aspect, the invention contemplates a pharmaceutically acceptable formulation. In one embodiment, the formulation includes levodopa, about 0.1% to about 6% by weight carbidopa, about 1% to about 25% by weight of a component selected from the group consisting of arginine, meglumine, and a combination thereof, and at least one o-quinone scavenger. In another embodiment, the formulation includes about 8% to about 16% (e.g., about 11% to 15% or about 12% to about 14%) by weight levodopa, about 1% to about 4% by weight carbidopa, about 0.1% to about 40% by weight of a component selected from arginine, meglumine, and a combination thereof, and at least one o-quinone scavenger. In either of these embodiments, the pharmaceutically acceptable formulation can have less than about 1.0, 0.75, 0.5, 0.25, 0.1, 0.05, or 0.025 µg/ml of hydrazine, e.g., as determined by a gas chromatography-mass spectrometry (GCMS) method. In particular embodiments, the formulation has less than about 0.1 or 0.05 µg/ml of hydrazine or about 0.1 to about 0.5 µg/ml of hydrazine, e.g., as determined by a GCMS method.

The formulation may include an o-quinone scavenger selected from the group consisting of ascorbic acid or a salt thereof, L-cysteine, NAC, glutathione, diacetylcystine and/or a salt thereof, and a combination thereof. The formulation may further include about 0.1% to about 10% by weight ascorbic acid or a salt thereof and a component selected from the group consisting of about 0.01% to about 1% by weight of NAC, about 0.01% to about 1% by weight L-cysteine, about 0.001% to about 1% by weight glutathione, and about 0.001% to about 1% by weight diacetylcystine or a salt thereof.

In another aspect, the invention contemplates a pharmaceutically acceptable formulation including (a) carbidopa (e.g., about 0.1% to about 10% carbidopa); (b) ascorbic acid or a salt thereof; and (c) one of L-cysteine, NAC, glutathione, and diacetylcystine, or a salt thereof. The formulation may include less than 1.0, 0.75, 0.5, 0.25, 0.1, 0.05, or 0.025 µg/ml of hydrazine, e.g., as determined by a GCMS method. In particular embodiments, the formulation has less than about 0.1 µg/ml of hydrazine, less than about 0.05 µg/ml of hydrazine, or about 0.1 to about 0.5 µg/ml of hydrazine, e.g., as determined by a GCMS method. The formulation may include about 0.1% to 10% (e.g., 0.3% to about 2%, about 0.5%, about 1.0% to about 1.3%, about 1.2%, or about 1.3%) by weight ascorbic acid. The formulation may include about 0.01% to about 1% (e.g., about 0.1% to about 0.6%, about 0.3%, about 0.4%, about 0.5%, about 0.6%, or about 0.8%) by weight L-cysteine, or a salt thereof. The formulation may include about 0.1% to about 10% (e.g., about 0.1% to about 6%, about 0.1% to about 4%, about 0.6% to about 1.4%, about 1.2% to about 4%, about 0.75%, about 1.4%, about 3%, or about 3.3%) by weight carbidopa. The formulation may include about 0.1% to about 10% (e.g., about 0.4% to about 0.6%, about 0.4% to about 1%, about 0.5%, or about 1.2%) by weight ascorbic acid, or a salt thereof. The formulation may include about 0.01% to about 1% (e.g., about 0.1% to about 1%, about 0.3%, about 0.4%, about 0.5%, about 0.6%, about 0.7%, or about 0.8%) by weight L-cysteine or NAC. The composition may include less than 4% (e.g., less than 2%, 1%, 0.5%, 0.1%, 0.05%, or 0.01%) by weight levodopa or may not include levodopa. In certain embodiments, the composition includes levodopa (e.g., about 2% to about 16%, about 2% to about 8%, about 8% to about 16%, about 6%, about 12% to about 15%; about 2% to about 16%, about 12%, or about 13% by weight levodopa). The composition may further comprise arginine, meglumine, or a combination thereof, for example, about 0.1% to about 40%, about 1% to about 25%, about 10% to about 25%, about 12% to about 40%, about 32% to about 42%, or about 15% to about 16% by weight arginine, meglumine, or a combination thereof. The formulation may include the components in the following Table:

| Components | Exemplary Amount | Exemplary amount |
|---|---|---|
| Levodopa | 0-16% | 5-7% |
| Carbidopa | 0.1-6% | 0.6-1.5% |
| Arginine | 0.1-40% | 14-16% |

-continued

| Components | Exemplary Amount | Exemplary amount |
|---|---|---|
| Ascorbic acid or Na ascorbate | 0.1-10% | 0.3-0.7% |
| L-cysteine or NAC or glutathione | 0.01-1% | 0.3-0.5% |

In particular embodiments, the formulation includes about 2% to about 8% by weight levodopa, about 0.1% to about 3% by weight carbidopa, about 10% to about 25% by weight arginine, about 0.1% to about 10% (e.g., about 0.3% to about 2%) by weight ascorbic acid or salts thereof, and about 0.001% to about 5% by weight L-cysteine or a salt thereof. In other embodiments, the formulation includes about 8% to about 16% by weight levodopa, about 1% to about 4% by weight carbidopa, about 12% to about 40% by weight of a component selected from the group consisting of arginine, meglumine, and a combination thereof, about 0.1% to about 10% by weight ascorbic acid or a salt thereof, and about 0.001% to about 1% by weight L-cysteine or a salt thereof. In either of these embodiments, the formulation has less than about 0.5 or 0.1 µg/ml hydrazine (e.g., less than 0.05 or 0.01 µg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| L-cysteine or cysteine HCl | 0.1-2% | 0.3-0.5% |

| Components | Exemplary Amount | Exemplary amount |
|---|---|---|
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| L-cysteine or cysteine-HCl | 0.1-1% | 0.2-0.5% |

In other particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight NAC. In other embodiments, the formulation includes about 8% to about 16% by weight levodopa, about 1% to about 4% by weight carbidopa, about 12% to about 40% by weight of a component selected from the group consisting of arginine, meglumine, and a combination thereof, about 0.1% to about 10% by weight ascorbic acid or a salt thereof, and about 0.001% to about 1% by weight NAC. In either of these embodiments, the formulation has less than about 0.5 or 0.1 µg/ml hydrazine (e.g., less than 0.05 or 0.01 µg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |

-continued

| Components | Exemplary Amount | Exemplary amount |
|---|---|---|
| Ascorbic acid | 0.1-2% | 0.3-0.7% |
| NAC | 0.1-2% | 0.3-0.5% |

| Components | Exemplary Amount | Exemplary amount |
|---|---|---|
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| NAC | 0.1-1% | 0.2-0.5% |

In particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight glutathione. In other embodiments, the formulation includes about 8% to about 16% by weight levodopa, about 1% to about 4% by weight carbidopa, about 12% to about 40% by weight of a component selected from the group consisting of arginine, meglumine, and a combination thereof, about 0.1% to about 10% by weight ascorbic acid or a salt thereof, and about 0.001% to about 1% by weight glutathione. In either of these embodiments, the formulation has less than about 0.5 or 0.1 μg/ml hydrazine (e.g., less than 0.05 or 0.01 μg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| Glutathione | 0.1-2% | 0.3-0.5% |

| Components | Exemplary Amount | Exemplary amount |
|---|---|---|
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| Glutathione | 0.1-1% | 0.2-0.5% |

In particular embodiments, the formulation includes about 2% to about 8% by weight levodopa, about 0.1% to about 3% by weight carbidopa, about 10% to about 25% by weight arginine, about 0.1% to about 10% by weight ascorbic acid or a salt thereof, and about 0.001% to about 5% by weight diacetylcystine or a salt thereof. In other embodiments, the formulation includes about 8% to about 16% by weight levodopa, about 1% to about 4% by weight carbidopa, about 12% to about 40% by weight of a component selected from the group consisting of arginine, meglumine, and a combination thereof, about 0.1% to about 10% by weight ascorbic acid, and/or a salt thereof, and about 0.001% to about 1% by weight diacetylcystine or a salt thereof. In either of these embodiments, the formulation has less than about 0.5 or 0.1 μg/ml hydrazine (e.g., less than 0.05 or 0.01 μg/ml hydrazine), as determined by GCMS. The formulation may include the components in the following Tables:

| Components | Exemplary Amount | Exemplary amount |
|---|---|---|
| Levodopa | 4-8% | 5-7% |
| Carbidopa | 0.5-2% | 0.6-1.5% |
| Arginine | 13-18% | 14-16% |
| Ascorbic acid | 0.1-2% | 0.3-0.7% |
| Diacetylcystine | 0.1-2% | 0.3-0.5% |

| Components | Exemplary Amount | Exemplary amount |
|---|---|---|
| Levodopa | 10-15% | 12-15% |
| Carbidopa | 1.2-4% | 2-4% |
| Arginine/meglumine or a combination thereof | 25-40% | 30-38% |
| Ascorbic acid or sodium ascorbate | 0.1-2% | 0.3-0.7% |
| Diacetylcystine | 0.1-1% | 0.2-0.5% |

The formulation of any of the above embodiments may include a surfactant. The surfactant may be any of one of polysorbate 20, 40, 60, and 80, or a combination thereof. In particular embodiments, the formulation includes about 0.01% to about 5% surfactant (e.g., polysorbate 80) or about 0.1% to 0.5% surfactant (e.g., polysorbate 80). In more particular embodiments, the formulation includes about 0.3% surfactant (e.g., polysorbate 80).

The formulation of any of the above embodiments may include about 11% to about 15% by weight levodopa. For example, the formulation may include about 12% to about 14% by weight levodopa (e.g., about 12% or about 13.2% levodopa).

The formulation of any of the above embodiments may include about 0.6% to about 4%, or 0.8% to about 3%, or about 1.2% to about 4%, by weight carbidopa. For example, the formulation may include about 2.5% to about 3.5% (e.g., about 3.0% or 3.3%) by weight carbidopa.

The formulation of any of the above embodiments may include about 25 to about 40% (e.g., about 32% to about 40%, about 32%, or about 36%) by weight of a component selected from the group consisting of arginine, meglumine, and a combination thereof. For example, the formulation may include 32% arginine, 32% meglumine, 36% arginine, or 36% meglumine.

The formulation of any of the above embodiments may, after storage for 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years, at 25° C., 2-8° C. or at −20° C., have less than about 0.1 μg/ml of hydrazine, as determined by GCMS.

The formulation of any of the above embodiments may have less than about 5% (e.g., less than 4%, 3%, 2%, 1%, 0.5%, 0.3%, 0.2%, 0.1% or 0.05%) by weight 3,4-dihydroxyphenyl-2-methylpropionic acid (Degradant RRT 1.4), relative to the amount of carbidopa, as determined by HPLC.

The formulation of any of the above embodiments may, after storage for 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years at 25° C., have less than 1% (e.g., less than 0.75%, 0.6%, 0.5%, 0.4%, 0.3%, 0.25%, 0.2%, 0.1%, 0.05%, or 0.01%) by weight 3,4-dihydroxyphenyl-2-methylpropionic acid, as determined by HPLC. In other embodiments, the formulation may, after storage for 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years, at 2-8° C., have less than 0.5% (e.g., less than 0.3%, 0.2%, 0.1%, or 0.01%) by weight 3,4-dihydroxyphenyl-2-methylpropionic acid, as determined by HPLC. In other embodiments, the formulation may, after storage for 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years, at −20° C., have less than 0.2% (e.g., less than 0.15%, 0.1%, 0.05%, or 0.01%) by weight 3,4-dihydroxyphenyl-2-methylpropionic acid, as determined by HPLC.

The formulation of any of the above embodiments may be in a form selected from the group consisting of liquid, gel, cream, solid, film, emulsion, suspension, solution, and aerosol (e.g., a liquid formulation).

In another aspect, the invention features a pharmaceutically acceptable liquid formulation including about 4% to about 8% (e.g., about 6%) by weight levodopa, about 0.1% to about 1.5% (e.g., about 0.6% to about 1.4%, about 0.75%, or about 1.4%) by weight carbidopa, about 10% to about 20% (e.g., about 15% to about 16%, about 15.2%, or about 15.6%) by weight arginine, and about 0.1% to about 1.5% (e.g., about 0.4 to about 1%, about 0.4% to about 0.6%, or about 0.5%) by weight ascorbic acid or a salt thereof, e.g., where the formulation, after 1 day at 25° C., or 30 days at 25° C. or after 180 days at 25° C., has less than about 1.0, 0.75, 0.5, 0.2, 0.1, or 0.05 µg/ml hydrazine, as determined by GCMS. The formulation may further include about 0.1% to about 0.7% (e.g., about 0.4% or about 0.5%) by weight of L-cysteine or NAC. In a particular embodiment, the formulation includes (a) about 0.4% to about 0.6% or about 0.4 to about 1% by weight ascorbic acid or a salt thereof and (b) about 0.1% to about 0.7% by weight of L-cysteine or NAC. In this aspect, the formulation may further include about 0.1% to about 0.5% (e.g., about 0.3%) by weight Tween-80.

In another aspect, the invention features a pharmaceutically acceptable liquid formulation including about 8% to about 16% (e.g., about 12% to about 15%, about 12%, or about 13.2%) by weight levodopa, about 1% to about 4% (e.g., about 3.0% or about 3.3%) by weight carbidopa, about 20% to about 42% (e.g., about 32% to about 42%, about 32%, or about 36%) by weight of a component selected from the group consisting of arginine, meglumine, and a combination thereof, and about 0.1% to about 1.5% (e.g., about 1.0% to about 1.4%, about 1.2%, or about 1.3%) by weight ascorbic acid or a salt thereof (e.g., sodium ascorbate), e.g., where the formulation, after 1, 2, 3, 4, 6, 8, 10, 12, 15, 18, 20, or 24 hours; 1, 2, 3, 5, 7, 10, 14, 21, 28, or 30 days; 1, 2, 3, 4, 6, 9, or 12 months; or 1, 1.5, 2, 2.5, or 3 years at 25° C., has less than about 1.0, 0.75, 0.5, 0.2, 0.1, or 0.05 µg/ml hydrazine as determined by GCMS. The formulation may further include about 0.1% to about 1% (e.g., about 0.1% to about 0.5%, about 0.3%, or about 0.5%) of L-cysteine or salt thereof (e.g., cysteine HCl) or NAC. In a particular embodiment, the formulation includes about 0.1% to about 0.5% of L-cysteine or NAC, and about 1.0 to about 1.4% by weight ascorbic acid or salt thereof.

In another aspect, the invention features a method for treating a disease (e.g., Parkinson's disease) or condition associated with loss of dopamine or dopaminergic neurons in a patient (e.g., a human or non-human animal, such as a mammal). The method includes administering to the patient an amount of the pharmaceutically acceptable formulation of any of the above aspects in an amount effective to the disease or condition in the patient. The method may include substantially continuous administration of the formulation.

In another aspect, the invention features a method of reducing the impurities in a formulation containing levodopa and carbidopa. The method includes (a) mixing together all powders (levodopa and/or carbidopa, L-arginine and/or meglumine, antioxidants); (b) adding the mixture of step (a) into pre-heated water or bringing the mixture to a temperature and for a time sufficient to dissolve the powders to form a solution; (c) cooling the solution to room temperature. The method may further include (d) adding additional water, antioxidants, and/or Tween-80, to the solution of step (c). In certain embodiments, the water in step (b) includes antioxidants prior to the mixing. The method may be used to produce a formulation of any one of the above aspects.

In another aspect, the invention features a kit including one, two, or more containers having a formulation of any one of the above aspects, where the formulation is present in an amount sufficient to treat a patient for a disease (e.g., Parkinson's disease) or condition resulting from decreased dopamine for at least 1, 2, 3, 4, or 5 days; 1, 2, 3 or 4 weeks; 1 to 12 (e.g., 1 to 2, 3, 4, 6, or 9) months; or 1, 1.5, 2, 3, 4, 5, 6, 7, 8, 9, 10, 15, 20 years, or more. In certain embodiments, the formulation is present in separate dosages.

In certain embodiments of any of the above aspects, the formulation, method, or kit further comprises or comprises the use, of a second agent. The second agent may be a catechol-O-methyl transferase (COMT) inhibitor, such as tolcapone or entacapone, or a pharmaceutically acceptable salt thereof.

BRIEF DESCRIPTION OF THE FIGURES

FIG. 1 is a graph depicting the main impurity ("Degradant") at retention time of about 14.5±0.2 min.

FIGS. 3A and 3B are graphs depicting typical MS/MS daughter scan (ion M/Z=179) spectrum (FIG. 3A) and parent (ion M/Z=105) spectrum (FIG. 3B) in collected main impurity peak from a formulation sample.

DETAILED DESCRIPTION

Figure 2A:
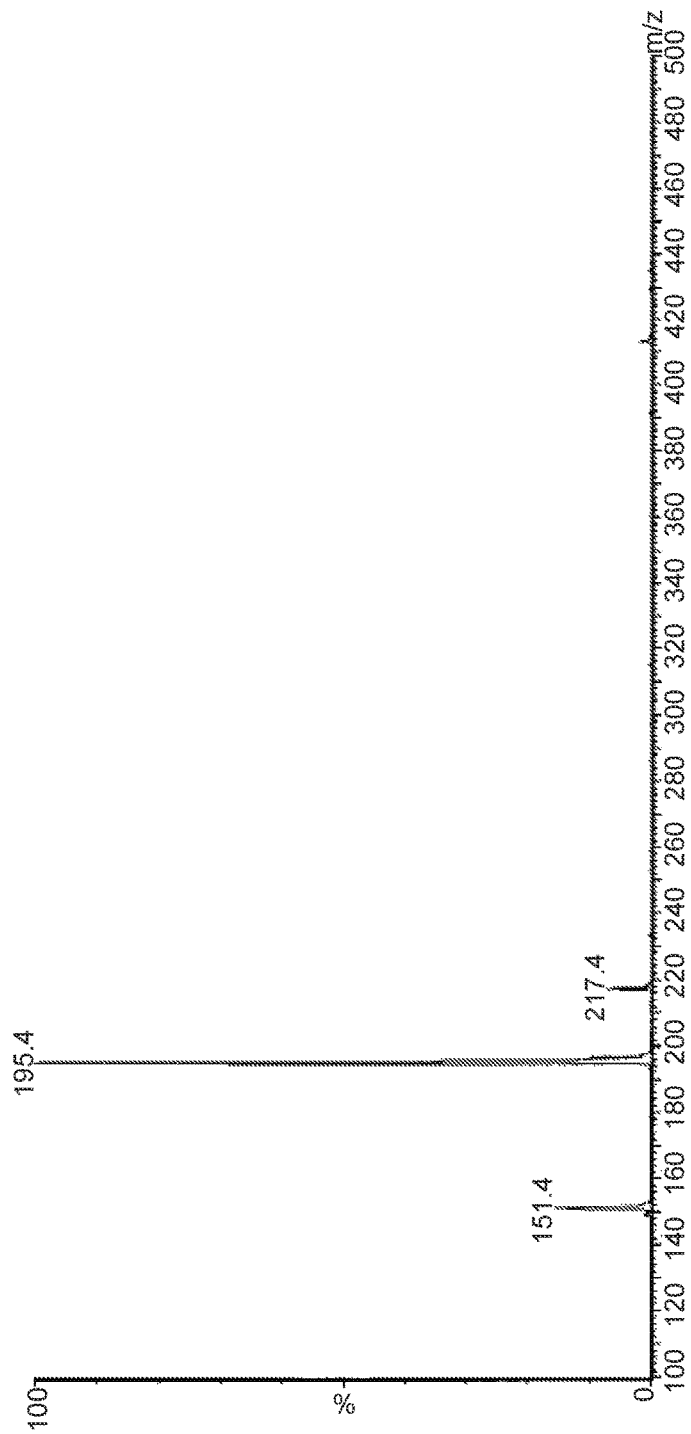
FIGS. 2A and 2B are graphs depicting typical MS spectrum in negative (FIG. 2A) and positive (FIG. 2B) mode of collected main impurity peak from a formulation sample.

Provided herein are, in an embodiment, carbidopa formulations and levodopa/carbidopa (LD/CD) formulations that can include, for example, one, two, or more antioxidant agents or o-quinone scavenger agents (e.g., ascorbic acid and L-cysteine, or ascorbic acid and N-acetylcysteine (NAC)). Such formulations, particularly those including two antioxidants (e.g., one of them being L-cysteine or NAC) and particularly when LD is present, can result in substantially lower levels of hydrazine, as compared to formulations with fewer antioxidants.

Disclosed formulations can include at least such two agents (e.g., ascorbic acid and L-cysteine, or ascorbic acid and NAC, or sodium ascorbate and L-cysteine, or sodium ascorbate and NAC). Such formulations can, e.g., reduce formation of undesired degradation products and/or provide substantially stable formulations. For example, provided herein are formulations that include carbidopa, having less than 0.1 µg/ml or less than 0.5 µg/ml hydrazine, as determined by GCMS and/or less than 5% or less than 1% by weight 3,4-dihydrooxyphenyl-2-methylpropionic acid (relative to the amount of carbidopa), as determined by HPLC.

By "substantially continuous" administration is meant that a dose of the formulation being administered not administered as a bolus, e.g., a pill taken orally or a bolus injection. For example substantially continuous administration can involve administration of a dosage at over a period of at least 10 minutes, 30 minutes, 1 hour, 2 hours, 4, hours, 6 hours, 8 hours, 12 hours, 15 hours, 18 hours, 21 hours, or 24 hours to administer a single dose. Substantially continuous administration can be achieved using a transdermal patch or a pump device that continuously administers the formulation to a patient over time.

The term "pharmaceutically acceptable carrier" or "pharmaceutically acceptable excipient" as used herein refers to any and all solvents, dispersion media, preservatives, antioxidants, coatings, isotonic and absorption delaying agents, and the like, that are compatible with pharmaceutical administration. The use of such media and agents for pharmaceutically active substances is well known in the art. The compositions can also contain other active compounds providing supplemental, additional, or enhanced therapeutic functions.

Pharmaceutically or pharmacologically "acceptable" include formulations, molecular entities, and compositions that do not produce an adverse, allergic or other untoward reaction when administered to an animal, or a human, as appropriate. For human administration, preparations should meet sterility, pyrogenicity, general safety and purity standards as required by, e.g., the U.S. FDA, and the EMA.

The term "pharmaceutical composition" as used herein refers to a composition or formulation comprising at least one active agent as disclosed herein formulated together with one or more pharmaceutically acceptable carriers.

The term "physiologically acceptable pH" is understood to mean a pH of, e.g., a formulation or composition that facilitates administration of the formulation or composition to a patient without significant adverse effects, e.g., a pH of about 4 to about 9.8 (for example, about 4±0.3 to about 9.5±0.3).

"Ambient temperature" as understood by a person of skill in the art is refers to a temperature of from about 10° C. to about 30° C. In particular embodiments, ambient temperature can be 25° C.

Percentages disclosed herein are by weight unless indicated otherwise.

Compositions and Formulations

Provided herein, in an embodiment, are formulations that include carbidopa (and/or an ester thereof) and arginine or meglumine (or a mixture thereof). The formulation can optionally include levodopa (and/or an ester thereof); one, two, or more o-quinone scavenger agents; and an antioxidant. Disclosed formulations can further include a surfactant (e.g., polysorbate 20, 40, 60, and 80, or a combination thereof).

In an embodiment, disclosed formulations can include about 0.1% to about 10% carbidopa, e.g., about 0.5% to about 8%, about 0.6% to about 5%, about 0.1% to about 1%, about 1% to about 2%, particularly about 0.75%, about 1.4%, or about 4%. For example, a disclosed formulation can include about 1% to about 3% by weight, about 2.5% to about 3.5% by weight, about 0.6% to about 4% by weight, or about 1.2% to about 4% by weight carbidopa. In certain embodiments, disclosed compositions include about 0.01% to about 6% by weight carbidopa, about 0.1% to about 6% by weight carbidopa, or about 1% about to 4% by weight carbidopa, e.g., about 0.6% to 4% or about 1.2% to 3% or 4% by weight carbidopa.

Disclosed formulations include arginine and/or meglumine (or a salt thereof and/or a combination thereof). For example, a disclosed formulation can include about 0.1% to about 42%, e.g., about 1% to about 10%, about 12% to about 18%, about 0.1% to about 40%, about 2% to about 7%, about 3.2%, about 3.4%, about 3.6%, about 3.7%, or about 4.6% arginine and/or meglumine. In other embodiments, disclosed formulations include about 10% to about 20%, about 10% to about 25%, 12% to about 18%, about 12.8%, about 14.8%, about 15.2%, about 15.5%, or about 18.5% arginine and/or meglumine (or a combination thereof). In certain embodiments, arginine, meglumine, a salt thereof, or a combination thereof are present at about 25% to about 40%, about 30% to about 38%, about 32% or about 36%.

In certain embodiments, disclosed formulations can also include a glucose amine which can, for example, replace some or all of the arginine present in the formulations.

Disclosed formulations described herein can optionally include levodopa. For example, in certain embodiments disclosed formulations include about 1% to about 20% levodopa, e.g., about 2% to about 8%, about 4% to about 7%, about 5%, or about 6%. In other embodiments, the formulations include about 8% to about 20%, about 8% to about 16%, about 10% to about 14%, about 11% to about 14%, about 12%, or about 13.2%. A disclosed formulation can have a molar ratio of carbidopa to arginine (or meglumine) of about 1:1 to about 1:25 or to about 1:35.

Disclosed formulations can include one, two, or more anti-oxidants or o-quinone scavenger agents. For example, a disclosed formulation can include one, two, or more of an agent each independently selected from the group consisting of ascorbic acid or a salt thereof (e.g., sodium ascorbate, calcium ascorbate, potassium ascorbate, ascorbyl palmitate, and ascorbyl stearate, particularly sodium ascorbate), and cysteine or a cysteine derivative (e.g., L-cysteine, N-acetylcysteine (NAC), glutathione, diacetylcystine, S-methyl-N-acetylcysteine amide, acetyl derivatives of S-methyl-N-acetylcysteine methylhydrazide, S-methylcysteine morpholineamide, and S-methyl-N-acetylcysteine morpholineamide, or a salt thereof). For example, a disclosed formulations can include an ascorbic acid, or salt thereof, and a cysteine derivative, such as NAC.

Disclosed formulations can include other antioxidants, such as di-tert-butyl methyl phenols, tert-butyl-methoxyphenols, polyphenols, tocopherols, and ubiquinones (e.g., caffeic acid).

Disclosed formulations can also include a tyrosinase inhibitor. Exemplary tyrosinase inhibitors include captopril, methimazole, quercetin, arbutin, aloesin, N-acetylglucoseamine, retinoic acid, α-tocopheryl ferulate, MAP (Mg ascorbyl phosphate), substrate analogues (e.g., sodium benzoate, L-phenylalanine), $Cu^{++}$ chelators, for example, $Na_2$-EDTA, $Na_2$-EDTA-Ca, DMSA (succimer), DPA (D-penicillamine), trientine-HCl, dimercaprol, clioquinol, sodium thiosulfate, TETA, TEPA, curcumin, neocuproine, tannin, and cuprizone.

Disclosed formulations can include ascorbic acid or salt thereof (e.g., sodium ascorbate). For example, disclosed formulations can include 0.1% to about 10% or more ascorbic acid (or salt thereof), or about 0.1% to about 2%, e.g., about 0.2% to about 1.5%, about 0.2% to about 2.0%, about 0.2% to about 2.5%, about 0.3% to about 1.2%, e.g., about 0.4%, about 0.5%, about 0.75%, about 0.85%, or about 1.0% by weight. For example, a disclosed formulation can include about 0.8% to about 1.3% or about 1% to about 2.5% by weight ascorbic acid or salt thereof. In a particular embodiment, a disclosed formulation can include 0.5% to about 0.85%, or, e.g., about 0.5%, about 0.75%, about 0.85%, about 1.0%, about 1.2%, or about 1.3% by weight sodium ascorbate or ascorbic acid.

In particular embodiments, disclosed formulations can include a bisulfite, e.g., sodium bisulfite or other sulfite salts, e.g., sodium hydrogen sulfite or sodium metabisulfite.

In an embodiment, disclosed formulations can include for example, NAC, L-cysteine, diacetylcystine, and/or glutathione. In particular embodiments, the formulations includes about 0.001% to about 5%, about 0.01% to about 5%, or about 0.1% to about 5%, about 0.001% to about 1%, or about 0.01% to about 1%, or about 0.1% to about 1% by weight of a compound selected from the group consisting of NAC, L-cysteine, diacetylcystine, and/or glutathione. For example, a disclosed formulations can include about 0.01% to about 5%, e.g., about 0.05% to about 1%, 0.1% to about 0.6%, about 0.1%, about 0.2%, about 0.3%, about 0.4%, or about 0.5% of NAC and/or L-cysteine. In a particular embodiment, a disclosed formulation includes about 0.4% or 0.5% NAC. In another particular embodiment, a disclosed formulation includes about 0.3%, about 0.4%, or about 0.5% L-cysteine.

For example, a disclosed formulations can include ascorbic acid (or a salt thereof) and a cysteine derivative, e.g., L-cysteine and/or NAC. In an exemplary embodiment, a disclosed formulation includes 0.1% to about 10% ascorbic acid (or salt thereof) and 0.001% to about 5% or about 0.001% to about 1% by weight L-cysteine and/or NAC and/or diacetylcystine and/or glutathione. In particular embodiments, the composition includes ascorbic acid and L-cysteine, sodium ascorbate and NAC, ascorbic acid and NAC, sodium ascorbate and L-cysteine, ascorbic acid and diacetylcystine, sodium ascorbate and diacetylcystine, ascorbic acid and glutathione, or sodium ascorbate and glutathione.

Contemplated formulations are liquid, and can include a surfactant. For example, polysorbate 20, 40, 60, or 80 may be present in a disclosed formulations at about e.g., about 0.01% to about 5%, about 0.1% to about 0.5%, e.g., about 0.3%. In particular embodiments, polysorbate 80 is present at about 0.3%.

Such formulations or solutions can have a pH that is pharmaceutically acceptable for subcutaneous administration, e.g., a pH of about 8 to about 10, for example, about 9.1 to about 9.8, e.g., 9.2 to 9.6 at 25° C.

Kits, Devices, and Articles

Contemplated herein, in part, is a patch suitable for transdermal or subcutaneous administration of an active agent in a formulation as disclosed herein, for example, including levodopa and carbidopa, and arginine. Such patches can have one or more compartments that can have the same or different formulations, for example, one compartment can have a disclosed formulation and another a different disclosed formulation, or a different active formulation. A dermal patch refers to any device that is capable of delivering one or more of the active agents forming a disclosed formulation through the skin or mucous membrane into the a patient.

In some embodiments, disclosed liquid formulations (e.g., comprising carbidopa, arginine, and optionally levodopa), can be provided in, e.g., a pre-filled cartridge or vial suitable for use by a patient or physician. For example, provided herein is a kit comprising a prefilled cartridge wherein a disclosed liquid formulation is disposed within the cartridge (e.g., a pre-filled cartridge having a single dose or a dose suitable for a single or multiple administration to a patient of a disclosed formulation and optionally instructions for use). For example, provided herein is a container, vial, pre-filled syringe or the like that can include about 1-10 ml of a disclosed formulation. For example, a contemplated kit can include one, two, or more pre-filled vial, container or syringe having an amount of a disclosed liquid formulation suitable for filling a syringe pump or patch pump, e.g., a vial, container, or syringe having about 1-6 ml, 2-5 ml, 1-2 ml, or 4-10 ml of a disclosed formulation.

The invention also contemplates kits that include formulations of the invention that take advantage of their increased stability. These kits can include a supply of a formulation of the invention sufficient for at least 1, 2, 3, 4, or 5 days; 1, 2, 3 or 4 weeks; 1, 2, 3, 4, 6, or 9 months; or 1 or 1.5 years of administration to a patient, which can be packaged, for example, into suitable dosage (e.g., unit dosage) formulations. These kits can optionally include instructions for their use. A kit for daily use for example, can include one, two or more containers or vials of a disclosed formulation, an infusion set, and a disposable patient delivery units (e.g. syringe).

Preparation of Compositions

Disclosed formulations or compositions can be prepared by mixing arginine and/or meglumine in amounts as disclosed above with levodopa and/or carbidopa, and optionally anti-oxidant(s), e.g., to form a powder mixture. Water can be added to the mixture to form a suspension. The water can be pre-heated or the suspension can be heated at a temperature and for a time sufficient to dissolve the mixture, e.g., to about 40° C. to about 100° C., or to about 40° C. to 80° C., or to about 60° C. to 90° C., e.g., 65±5° C. or 72±5° C. or 73±3° C., e.g., by adding pre-heated water and/or by placing the mixture in a hot (e.g., 65±5° C. or 72±5° C. or 73±3° C.) water bath (e.g., for up to about 10 minutes, for about 3 minutes, for about 5 minutes, or for about 10, 20, 30, 40, 50, 60 minutes, or more) to form a solution, with optional stirring. This is followed by cooling the solution to form the composition. $N_2$ can be provided the head space of the container. For example, the mixture can then be removed from the hot water bath and cooled to room temperature, and adding, e.g., immediately thereafter, an optional anti-oxidant(s) under $N_2$ atmosphere and subsequent stirring. A preparation such as that above, e.g., where levodopa and/or carbidopa, and arginine are mixed together as powders first, and a suspension formed with water and then heated can result in a more stable solution, as compared to a preparation that includes a stepwise preparation of individual water suspensions of ingredients and later combination. Specific methods of preparation are described in Example 1 below.

Disclosed formulations can be sterilized, e.g., using 0.2 μm filters such as filters with nylon or PVDF membranes. In another embodiment, the preparation of disclosed formulations has fewer undesirable by-products when pre-heated water is added as disclosed above, as compared to a formulation prepared without the addition of pre-heated water. In another embodiment, the levodopa and/or carbidopa cannot dissolve unless the preparation procedure disclosed is used. Such disclosed preparations as above can provide a more stable formulation as compared to a formulation prepared without adding hot water or heating. Disclosed preparations can provide a more stable formulation as compared to a formulation prepared without adding antioxidants prior to heating.

Methods of Treatment

In another aspect, the present invention contemplates a method for treatment of a disease or disorder, such as a neurological disorder (e.g., a disorder associated with reduced dopamine or loss of dopaminergic neurons) or a movement disorder, comprising administering a formulations described herein. The method can include substantially continuously administering the formulation.

Also provided herein are methods of treating a neurological disorder (e.g., a disorder associated with reduced dopamine or death of dopaminergic neurons) or a movement disorder that include substantially continuous administration of a formulation described herein.

Without limiting, the pharmaceuticals compositions as described above can be used for treating a neurological disorder (e.g., a disorder associated with reduced dopamine or death of dopaminergic neurons) or a movement disorder that include acute and immediate administration such as inhalation or injection.

In some embodiments, compositions comprising levodopa (e.g. a disclosed liquid composition) may be administered at a rate of about 0.16 ml/hour/site to about 0.24 ml/hour/site, or, e.g., about 0.01 ml/hour to about 0.4 ml/hour/site. Such rates may be constant throughout the day and night or varied according to patient's need, for example, may reflect a patient resting or sleeping schedule and waking or higher activity level schedule. For example, liquid compositions such as those disclosed herein (e.g., including levodopa) may be administered at a rate of about 0.32 ml/hour/site in the morning (e.g., for about 2-4 hours before waking), about 0.24 ml/hour/site during the daytime or activity time, (e.g., for about 10 to about 12 hours), and/or about 0.08 ml/hour/site at rest or at night. In another embodiment, liquid composition such as those disclosed herein may be administered, e.g., intraduodenally, at a rate of about 1.0 ml/hour during the daytime or activity time (e.g., for about 2-3 hours before waking and for about 10 to about 12 hours thereafter), and 0 to about 0.5 ml/hour at rest or at night. In another embodiment, liquid compositions such as disclosed herein (e.g., comprising levodopa and arginine), may be administered at a rate of about 1.25 ml/hour (e.g., about 1.25±0.5 ml/hour during the daytime or activity time (e.g., for about 2-3 hours before or after waking and for about 10 to about 14 hours thereafter) and 0 to about 0.5 ml/hour (e.g. about 0.5±0.25 ml/hour) at rest or night. In further embodiments, such compositions may be administered at a rate of about 0.1 to about 1000 µl/hour/site; or at a volume of about 2 to about 10 ml/24 hour/site, preferably about 4 to about 6 ml/24 hour/site; or at a dose of about 80 to about 800 mg levodopa/day and about 20 to about 200 mg carbidopa/day; or at a rate of about 240 to about 360 mg levodopa and about 60 to about 90 mg carbidopa/day/site.

Contemplated administration, following the disclosed methods, typically can be carried out over a defined time period (usually weeks, months, or years). Administration can be effected by any appropriate route including, but not limited to, subcutaneous, oral routes, intravenous routes, intramuscular routes, intradermal routes, subcutaneously, intratracheally, intrathecally, intraduodenally, transdermally, inhalation, and/or direct absorption through mucous membrane tissues.

The disease or disorder characterized by reduced levels of dopamine in a patient contemplated herein are neurological or movement disorders including restless leg syndrome, Parkinson's disease, secondary parkinsonism, Huntington's disease, Shy-Drager syndrome, and conditions resulting from brain injury including carbon monoxide or manganese intoxication. Methods for treating such disorders in a patient in need thereof are provided, for example, by administering (e.g., subcutaneously) a disclosed formulation. In one embodiment, the disease to be treated is Parkinson's disease.

In an embodiment, substantially continuously administering using, e.g., a liquid formulation can be via a pump for subcutaneous infusion (insulin pump) at an average rate of about 10-1000 µl/hour (e.g., 10-250 µl/hour), about 300±100 µl/hour, or about 200±40 µl/hour continuously for 24 hours; about 440±200 µl/hour or about 200±50 µl/hour continuously for 16 hours (during waking hours) and at night (e.g., for 8 hours, about 0 to 80 µl/hour or 0 to 200 µl/hour or via a pump or a transdermal patch. Substantially continuously administering the formulation in to a patient can be doubled or tripled by using more than one pump or site of infusion. In an embodiment, substantially continuously administering using, e.g., a liquid formulation can be at an average rate of about 0.2-2 µl/hour, or about 1±0.5 µl/hour continuously for 24 hours; about 1.0±0.5 µl/hour continuously for 16 hours (during waking hours) and at night (e.g., for 8 hours, about 0 to 0.5 µl/hour via a pump or transdermal patch, or combination of delivery devices that are suitable for, e.g., subcutaneous, intravenous, intrathecal, and/or via the duodenum).

The invention now being generally described, it will be more readily understood by reference to the following examples which are included merely for purposes of illustration of certain aspects and embodiments of the present invention, and are not intended to limit the invention in any way.

EXAMPLES

Example 1 Formulation Preparation Procedure

Levodopa (LD) and carbidopa (CD) formulations can be prepared as follows.

Method #1 (L-Arg solution): L-Arg and Na-Bis (Na-bisulfite) were dissolved in water. The solution was added to the LD and CD powders. The mixture was heated with stirring for 13 min at 75° C. until fully dissolved. The LD/CD solution was kept at room temperature (RT) for 10 min to cool down.

Method #2 (all powders together): All powders (LD, CD, and L-Arg) were weighed, and water with Na-Bis was added. The suspension was heated with stirring for 13 min at 75° C. until fully dissolved. The LD/CD solution was kept at RT for 10 min to cool down.

Method #3 (same as #2 without Na-Bis pre-heating): All powders (LD, CD, and L-Arg) were weighed together and water was added. The suspension was heated with stirring for 13 min at 75° C. until fully dissolved. The LD/CD solution was kept at RT for 10 min to cool down.

Method #4 (preparation in steps): LD and the respective amount of L-Arg were weighed; water and Na-Bis solution were added. The suspension was heated for 7 min at 75° C. until fully dissolved, followed by 7 min at RT. CD and the respective amount of L-Arg were weighed and added to the LD/Arg solution at 60° C. until fully dissolved. Finally, extra L-Arg was added.

Method #5 (same as #4 without Na-Bis pre-heating): LD and the respective amount of L-Arg were weighed; water was added. The suspension was heated for 7 min at 75° C. until fully dissolved followed by 7 min at RT. CD and the respective amount of L-Arg were weighed and added to the LD/Arg solution at 60° C. until fully dissolved. Finally, extra L-Arg was added.

After cooling down, all formulations from all methods were divided in to 3 vials, and water, Na-Bis solution, or Na-Bis-Arg solution was added to each vial.

Example 2: Identification of the Main Degradant in Formulations Containing Carbidopa Liquid formulations with levodopa, carbidopa, and arginine were prepared using the procedure outlined in Example 1, and HPLC analysis was performed according to APH stability-indicating analytical method for carbidopa levodopa formulations with Agilent 1100 system.

The HPLC system used herein includes the following components manufactured by Agilent: pump system (model G1311A), diode array detector (model G1315B), autosampler (model G1329A), degasser (model G1379A), thermostat (model G1330B), thermostatted column compartment (model G1316A). The column employed was a new Synergi 4μ Fusion-RP 80A, 250×4.6 mm (Phenomenex®).

HPLC working conditions:
Wavelength: 280 nm
Flow rate: 1.0 ml/min
Inj. volume: 10 μl
Column temperature: 30° C.
Thermostat temperature: 4° C.
Stop time: 27 min
Pressure: 105 bar
Mobile phase preparation:
Solvent A: Acetonitrile
Solvent B: 20 mM potassium dihydrogen phosphate, pH=2.4
The mobile phase B was prepared by weighing 2.72 g/L of potassium dihydrogen phosphate. pH was adjusted to 2.4 by addition of $H_3PO_4$.
Gradient:

| Time  | Solvent A | Solvent B | Flow |
|-------|-----------|-----------|------|
| 0     | 5         | 95        | 1.0  |
| 5     | 5         | 95        | 1.0  |
| 15    | 60        | 40        | 1.0  |
| 20    | 60        | 40        | 1.0  |
| 20.01 | 5         | 95        | 1.2  |
| 27    | 5         | 95        | 1.2  |

Diluent:
0.1M HCl/MeOH 9:1
(8.3 ml HCl 37% to 1 L)-->0.1 M HCl
STD LDOPA=100.00 mg/100 ml
STD CDOPA=25.00 mg/100 ml
Calibration curve:

| STD stock sol. 1000/250 ppm | Volumetric bottle, ml | Final concentr. LD/CD ppm |
|------------------------------|----------------------|---------------------------|
| NA                           | 10                   | 1000/250                  |
| 5000 from stock              | 10                   | 500/125                   |
| 5000 from 500/125            | 10                   | 250/62.5                  |
| 1000 from stock              | 10                   | 100/25                    |
| 5000 from 100/25             | 10                   | 50/12.5                   |
| 1000 from 100/25             | 10                   | 10/2.5                    |

One ml of the sample (levodopa/carbidopa formulation) was transferred to a 25 ml amber volumetric glass flask and filled to volume with diluent (0.1 M HCl/MeOH 9/1). The sample was degraded with hydrogen peroxide.

The impurity was observed at retention time of about 14.5±0.2 min (FIG. 1). To ensure that the peak observed is actually the compound of interest, the main degradant peak was collected from analytical HPLC, evaporated under nitrogen stream and reconstituted with diluent. Obtained samples were tested by HPLC/MS.

Figure 2B:
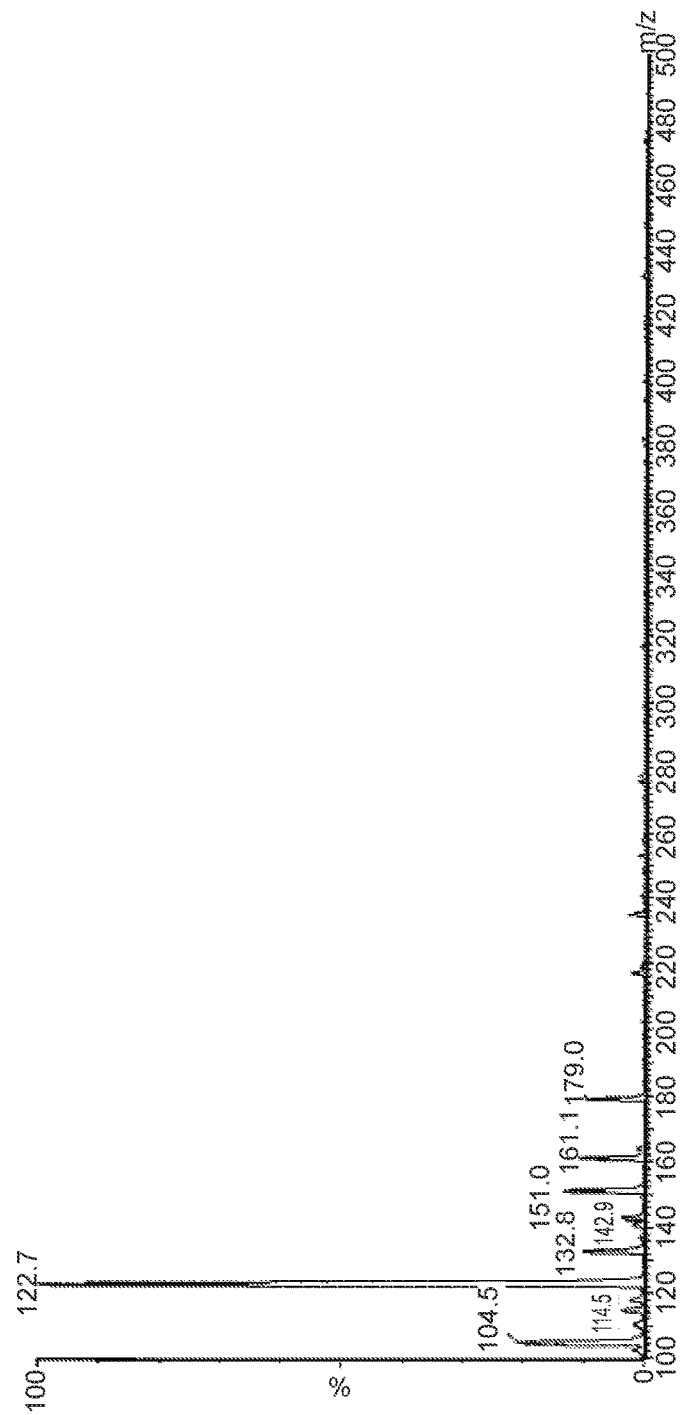

Initially, an MS scan analysis was applied (FIGS. 2A and 2B). The unknown compound shows clear and intensive signal in negative mode and much nosier signal in positive mode. Therefore it was expected to be more a proton donor than acceptor. The base peak in negative mode was M/Z=195 Da that was suspected as (M−H). The mass difference between this ion and peak M/Z=217 is 22 and that should be the sodium adduct. This is the evidence of the presence of carboxyl or/and phenol groups. Due to this fact, the molecular weight was proposed to be 196 Da.

The peak M/Z=197 (M+H+)+ was not found in positive mode, but the peak M/Z=197 (M−H2O)+ is observed. This is typical for oxygen containing molecule.

Figure 3A:
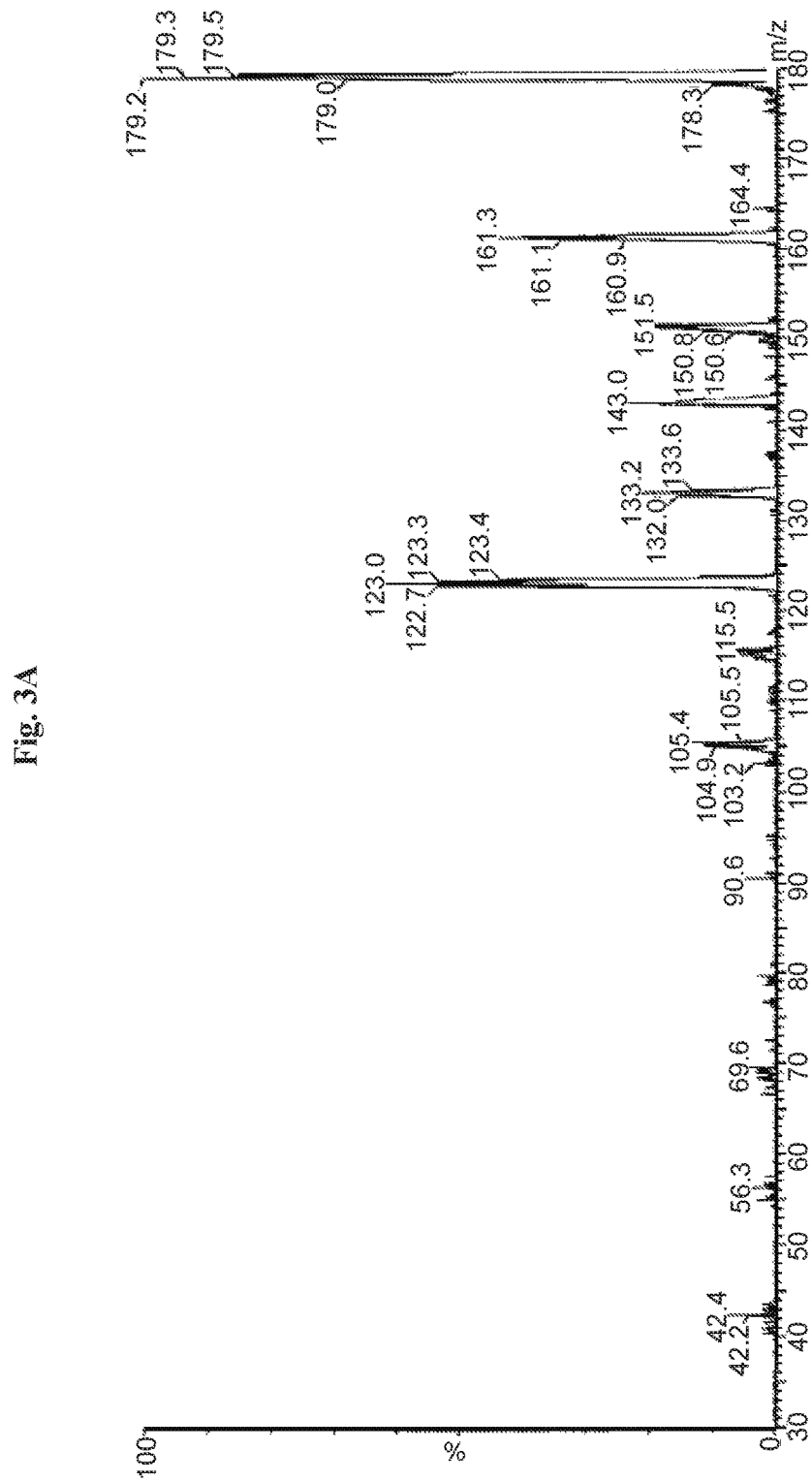

The daughter and parent MS/MS was performed as well to define molecular structure. Peaks observed in positive mode with M/Z=179, 161, 151, 133, 123, 105 were found to be relative. They were defined as in-source fragment ions arising from the molecular ion with M/Z=197. The typical MS and MS/MS spectra are shown on figures (FIGS. 3A and 3B).

The chemical formula of the degradant compound is $C_{10}H_{12}O_4$; with a molecular structure given by 3-(3,4 dihydroxyphenyl)-2-methylpropanoic acid.

Example 3: Effect of Ascorbic Acid with or without EDTA on LD/CD Formulation Stability Liquid formulations were prepared by weighing all powders (LD, CD, EDTA, ascorbic acid, and L-Arg) and adding water pre-heated to 73±3° C. The suspension was put in a water bath at 73±3° C. and stirred for 10 min until fully dissolved. LD/CD solution was kept at RT for 10 min to cool down. Solutions were divided into glass vials and kept at +25° C. and at −20° C. for the indicated period of time. Prior to analyses, frozen vials were placed at RT until fully thawed. Formulations were then mixed and subjected to stability analyses. The effect of ascorbic acid with or without EDTA on stability of LD/CD formulations was measured by HPLC. The levels of the degradant presented in Tables A and B indicate the level of stability of LD/CD formulations.

TABLE A

| LD/CD | L-Arginine (%) | Ca-EDTA-Na$_2$ (%) | Ascorbic acid (%) | t = 0 Degradant | Total (%) |
|-------|----------------|---------------------|-------------------|-----------------|-----------|
| 6/1.4 | 14.80          | 0.2                 | 1.0               | 0.13            | 0.76      |
| 6/1.4 | 14.80          | 0                   | 1.0               | 0.08            | 0.44      |

TABLE B

| LD/CD | L-Arginine (%) | Ca-EDTA-Na$_2$ (%) | Ascorbic acid (%) | t = 0 Degradant | Total (%) | t = 1 w (25°) De-gradant | Total (%) |
|-------|----------------|---------------------|-------------------|-----------------|-----------|---------------------------|-----------|
| 6.0/1.4 | 14.80        | 0.2                 | 1.0               | 0.054           | 0.64      | 0.16                      | 0.79      |
| 6.0/1.4 | 14.80        | 0                   | 1.0               | 0.046           | 0.49      | 0.15                      | 0.49      |

Tables A and B indicate that EDTA did not have a significant effect on the stability of LD/CD formulations.

Example 4: Effect of L-Cysteine on the Stability of Solutions Containing CD

Liquid formulations were prepared by weighing all powders (LD, CD, L-cysteine, ascorbic acid, and L-Arg) and adding water pre-heated to 73±3° C. The suspension was put in a water bath at 73±3° C. and stirred for 10 min until fully dissolved. LD/CD solution was kept at RT for 10 min to cool down. For CD formulations, CD, L-cysteine, and ascorbic acid were weighed, and pre-heated water (60° C.) was added. Solutions were divided into glass vials and kept at +25° C. and at −20° C. for the indicated period of time. Prior to analyses, frozen vials were placed at RT until fully thawed. Formulations were then mixed and subjected to stability analyses. The effect of L-cysteine on the stability of carbidopa formulations when stored at 25° C., either exposed to air or maintained under anaerobic conditions ($N_2$), was analyzed using HPLC. The levels of the degradant presented in Table C point toward the level of stability of carbidopa formulations.

TABLE C

| LD/CD | L-arginine | Ascorbic acid (%) | L-Cysteine (%) | | Degradant t = 0 | t = 5 days | t = 5 weeks |
|---|---|---|---|---|---|---|---|
| 6/1.4 | 14.8 | 0.5 | 0.1 | $N_2$ | 0.08 | 0.22 | 0.28 |
|  |  |  |  | $O_2$ |  | 0.59 | 0.77 |
|  |  | 0.5 | 0.2 | $N_2$ | 0.08 | 0.20 | 0.25 |
|  |  |  |  | $O_2$ |  | 0.36 | 0.32 |
|  |  | 0.5 | 0.4 | $N_2$ | 0.00 | 0.14 | 0.14 |
|  |  |  |  | $O_2$ |  | 0.14 | 0.17 |
| 0/4 | 4.6 | 0.5 | 0.1 | $N_2$ | 0.05 | 0.16 |  |
|  |  |  |  | $O_2$ |  | 1.42 |  |
|  |  | 0.5 | 0.2 | $N_2$ | 0.05 | 0.16 |  |
|  |  |  |  | $O_2$ |  | 0.56 |  |
|  |  | 0.5 | 0.4 | $N_2$ | 0.04 | 0.15 |  |
|  |  |  |  | $O_2$ |  | 0.35 |  |

As Table C indicates, ascorbic acid with 0.1% L-cysteine was sufficient to inhibit degradant formation in formulations containing carbidopa (with or without levodopa) when kept under anaerobic conditions at 25° C. for at least 5 weeks. We can further deduce from Table C, that L-cysteine reduced degradant formation under aerobic conditions at 25° C. in a dose-dependent manner.

In formulations containing carbidopa and 0.4% L-cysteine, degradant formation was inhibited during the preparation of the formulation. These formulations were stable for at least 5 weeks at 25° C. under both aerobic and anaerobic conditions. Formulations containing carbidopa are more stable when they also contain LD upon exposure to air.

Example 5: Effect of L-Cysteine on 6/1.4% Levodopa/Carbidopa Formulation Stability Liquid formulations were prepared as described in Example 3. The effect of L-Cysteine on the stability of 6/1.4% levodopa/carbidopa solutions at 25° C. was analyzed using HPLC. The levels of the degradant presented in tables D, E, F, and G point toward the level of stability of referenced formulations.

TABLE D

| LD/CD (%) | L-Arginine (%) | Ascorbic Acid (%) | L-Cysteine (%) | Degradant t = 0 |
|---|---|---|---|---|
| 6/1.4 | 14.8 | 0.5 | 0.2 | 0.02 |
|  |  | 0.75 | 0.0 | 0.16 |

TABLE E

| LD/CD (%) | L-arginine (%) | Ascorbic acid (%) | L-Cysteine (%) | Degradant t = 0 | t = 5 d | t = 5 wk |
|---|---|---|---|---|---|---|
| 6/1.4 | 14.8 | 0.75 | 0 | 0.49 | 0.93 | 1.08 |
|  |  |  | 0.1 | 0.10 | 0.35 | 0.32 |
|  |  | 0.50 | 0.1 | 0.16 | 0.28 | 0.45 |
|  |  |  | 0.4 | 0.00 | 0.15 | 0.13 |

TABLE F

| LD/CD (%) | L-arginine (%) | Ascorbic acid (%) | L-Cysteine (%) | Degradant t = 0 | t = 1 d | t = 4 d |
|---|---|---|---|---|---|---|
| 6/1.4 | 14.8 | 0.5 | 0.4 | 0.00 | 0.00 | 0.27 |
|  |  |  | 0.1 | 0.25 | 0.69 | 1.26 |
|  |  | 0.75 | 0.1 | 0.23 | 0.56 | 0.85 |
|  | 15.1 | 1.0 | 0.2 | 0.00 | 0.26 | 0.51 |

TABLE G

| LD/CD (%) | L-arginine (%) | Ascorbic acid (%) | L-Cysteine (%) | Degradant t = 0 | t = 10 d | t = 3 weeks | t = 3 months |
|---|---|---|---|---|---|---|---|
| 6/1.4 | 14.8 | 0.5 | 0.1 | 0.15 | 0.43 | 0.46 | 0.87 |
|  |  | 0.75 | 0.0 | 1.01 | 1.40 | 1.37 | 2.00 |

Results show that levodopa/carbidopa formulations were more stable with both ascorbic acid and L-cysteine, as compared to ascorbic acid alone, suggesting that L-cysteine and ascorbic acid have a synergistic effect in preventing degradant formation. Other results showed that L-cysteine alone had no effect at all (data not shown). Furthermore, L-cysteine inhibited degradant formation during formulation preparation and maintained the stability of the formulation for at least up to 5 weeks at 25° C., in a dose dependent manner. Increasing the amount of ascorbic acid reduces degradant formation, but this was significantly less efficient than the combination of ascorbic acid with L-cysteine.

Example 6: Effect of Tween-80 and Na-Ascorbate on Levodopa/Carbidopa Formulation Stability Liquid formulations were prepared by weighing all powders (LD, CD, L-Cysteine, ascorbic acid, Na-ascorbate and L-Arg) and adding water pre-heated to 73±3° C. The suspension was put in a water bath at 73±3° C. and stirred for 10 min until fully dissolved. LD/CD solution was kept at RT for 10 min to cool down. Then, Tween-80 was added. Solutions were divided in to glass vials and kept at +25° C. and at −20° C. for the indicated period of time. Prior to analyses, frozen vials were placed at RT until fully thawed. Formulations were then mixed and subjected to stability analyses. The effect of Tween-80 and Na-ascorbate on the stability of carbidopa/levodopa formulations was analyzed using HPLC. The levels of the degradant presented in table H point toward the level of stability of carbidopa/levodopa formulations.

TABLE H

| LD:CD (%) | L-Arginine (%) | Asc. acid: L-Cys (%) | Tw-80 (%) | Degradant t = 0 | Degradant t = 1 month |
|---|---|---|---|---|---|
| 6.0:1.5 | 14.8 | 0.5:0.4 | 0 | 0.07 | 0.08 |
| 6.0:1.5 | 14.8 | 0.5:0.4 | 0.3 | 0.10 | N/A |
| 6.0:1.5 | 14.8 | 0.5:0.4 | 0.75 | 0.15 | |
| 6.0:1.5 | 14.8 | 0.5:0.4 | 2.0 | 0.00 | |
| 6.0:1.5 | 14.8 | 0.75:0.1 | 0 | 0.26 | |
| 6.0:1.5 | 14.8 | 0.75:0.1 | 0.75 | 0.31 | |
| 6.0:1.5 | 14.8 | 0.75:0.2 | 0 | 0.14 | |
| 6.0:1.5 | 14.8 | 0.75:0.2 | 0.3 | 0.27 | |
| 6.0:1.5 | 14.8 | 0.75:0.2 | 0.75 | 0.24 | |
| 6.0:1.5 | 14.8 | 0.75:0.2 | 2.0 | 0.35 | |
| 7.5:1.5 | 18.5 | 0.75:0.2 | 0 | 0.19 | 0.26 |
| 7.5:1.5 | 18.5 | 0.75:0.2 | 0.75 | 0.35 | 0.45 |
| 7.5:1.5 | 18.5 | 0.85*:0.2 | 0 | 0.23 | 0.20 |
| 7.5:1.5 | 18.5 | 0.85*:0.2 | 0.75 | 0.25 | 0.27 |

*Sodium ascorbate

The results demonstrate that Tween-80 did not have an effect on degradant formation. It is also shown that the effect of L-cysteine on the stability of the formulations was dose dependent. Table H further shows that the effect of Na-ascorbate and ascorbic acid on the stability of the formulations and degradant formation was similar.

Example 7: Effect of Ascorbic Acid with or without L-Cysteine or NAC on Long Term Stability of Levodopa/Carbidopa Formulations Liquid formulations were prepared by weighing all powders (LD, CD, arginine, L-Cysteine or NAC, and ascorbic acid or Na-ascorbate) and by adding water pre-heated to 73±3° C. The suspension was put in a water bath at 73±3° C. and stirred until fully dissolved. LD/CD solution was kept at RT to cool down. Then Tween-80 was added. Solutions were divided into glass vials and kept at +25° C. and at −20° C. for the indicated period of time. Prior to analyses, frozen vials were placed at RT until fully thawed. Formulations were then mixed and subjected to stability analyses. The effect of ascorbic acid with or without L-cysteine or NAC on the stability of carbidopa/levodopa formulations was analyzed using HPLC. The levels of the degradant presented in Table I indicate the level of stability of carbidopa/levodopa formulations.

Example 8: Effect of Antioxidants on the Stability of Carbidopa Formulations

Liquid formulations with carbidopa and arginine were prepared as described above. The effect of antioxidants on the stability of carbidopa formulations was analyzed using HPLC. The levels of the degradant presented in Tables J and K point toward the level of stability of carbidopa formulations.

TABLE J

| 7 weeks at (−20° C.) | 1 0.1% Na Bisulfite | 2 0.075% Na Bisulfite | 3 0.4% Asc. + 0.2% L-Cys | 4 0.5% Asc. + 0.1% L-Cys |
|---|---|---|---|---|
| Methyl-Dopa | 0.15 | 0.15 | 0.15 | 0.15 |
| Unknown 2 | 0.18 | 0.17 | 0 | 0 |
| Degradant | 0.54 | 0.55 | 0 | 0.16 |
| Sum of all Impurities | 1.14 | 1.15 | 0.44 | 0.65 |

TABLE K

| | | Peak 14.3 min (degradant) | |
|---|---|---|---|
| | t = 0 | t = 3 weeks 2-8° C. | t = 3 weeks 25° C. |
| 2  4% CD – 3.7% L-Arg 0.075% sodium bisulfite | 0.30 | 1.12 ± 0.19 | 1.08 ± 0.07 |
| 3  4% CD – 4.62% L-Arg 0.4% ascorbic + 0.2% L-cysteine | 0.06 | 0.15 ± 0.01 | 0.29 ± 0.07 |
| 4  4% CD – 4.62% L-Arg 0.5% ascorbic + 0.1% L-cysteine | 0.11 | 0.44 ± 0.21 | 0.63 ± 0.39 |

The results in Tables J and K suggest that formulations containing ascorbic acid+L-cysteine were significantly more stable than the formulation containing Na-bisulfite (formulations 3 & 4 vs. formulations 1 & 2). The same amount of impurities were measured with 0.075 and 0.1% Na-bisulfite, suggesting that the maximum possible protection with Na-bisulfite was attained.

TABLE I

| LD/CD (%) | Ascorbic acid (%) | (NAC) (%) | Tween-80 (%) | Arginine (%) | Degradant −20° C. $T_0$ | 1 m | 2 m | 3 m | 6 m | 9 m | 12 m | 16.5 m | 25° C. 1 m | 2x F-T* (ambient) >3 m/>7 d |
|---|---|---|---|---|---|---|---|---|---|---|---|---|---|---|
| 5/1.15 | 0.75 | 0 | 0 | 12.8 | 0.55 | 0.6 | 0.75 | 0.9 | 1.0 | 0.8 | — | 1.0 | 1.2 | — |
| 6/1.4 | 0.75 | 0 | 0 | 14.8 | 0.4 | 0.45 | 0.45 | 0.6 | 0.5 | 0.8 | — | 0.6 | 0.6 | — |
| 6/1.4 | 0.5 | 0.4 | 0 | 14.8 | 0 | 0 | — | — | — | 0.25 | 0.15 | — | 0 | — |
| 6/1.4 | 0.5 | 0.4 | 0.3 | 15.5 | 0 | — | 0.1 | 0.2 | 0.2 | 0.2 | — | — | — | — |
| 6/1.4 | 0.5 | (0.5) | 0.3 | 15.5 | 0 | 0 | — | — | — | — | — | — | 0.2 | 0 |
| 6/0.75 | 0.5 | (0.5) | 0.3 | 15.2 | 0 | 0.1 | — | — | — | — | — | — | 0 | 0.2 |

*2xF/T - at least 2 freeze-thaw cycles after >3 m at −20° c., and >7 d at ambient temp.

The results presented in Table I suggest that formulations containing both ascorbic acid and L-cysteine or NAC are more stable than formulations having only ascorbic acid, at a) $T_0$, i.e., immediately following formulation preparation, b) for at least 9 months at −20° C., and c) at for least 1 month at ambient temperature.

In sum, the combination of ascorbic acid/L-cysteine is able to prevent degradant and other impurities formation, such as hydrazine (see other examples), while Na-bisulfite does not protect formulations containing carbidopa to the same extent.

Example 9: Effect of Various Antioxidants and Different Concentrations of Arginine on the Stability of Formulations Containing 4% CD Liquid formulations with carbidopa and arginine (Table L) were prepared as described above. The effect various antioxidants and different concentrations of arginine on the stability of formulations containing 4% CD, and stored under aerobic (air) or anaerobic ($N_2$) conditions, at ambient (25° C.) or cold (2-8° C.) temperature was evaluated using HPLC analysis. The levels of the degradant and total impurities as presented in Tables M and N, respectively, point toward the level of stability of carbidopa formulations.

TABLE L

|  | 1 | 2 | 3 |
|---|---|---|---|
| Carbidopa | 4.0 | 4.0 | 4.0 |
| L-Arginine | 4.6 | 4.6 | 3.7 |
| Ascorbic acid | 0.4 | 0 | 0 |
| L-Cysteine | 0.2 | 0 | 0 |
| Na bisulfite (5%) | 0 | 1.5 | 1.5 |
| Total solutes | 9.2 | 10.1 | 9.2 |
| Water | 90.8 | 89.9 | 90.8 |
| L-Arg (mM) | 265 | 265 | 212 |
| CD (mM) | 177 | 177 | 177 |
| Ratio L-Arg/CD | 1.5 | 1.5 | 1.2 |
| pH measured | 8.67 | 8.87 | 8.62 |

TABLE M degradant: Peak area (%)

|  |  |  | T = 1 week 2-8° C. |  | T = 1 week 25° C. |
|---|---|---|---|---|---|
|  |  | t = 0 | Air | N2 | Air |
| 1 | 0.4% ascorbic + 0.2% cysteine (CD:Arg 1.0:1.5) | 0.1 | 1.7 | 0.2 | 5.8 |
| 2 | 0.075% Bisulfite (CD:Arg 1.0:1.5) | 0.2 | 1.9 | 1.2 | 6.2 |
| 3 | 0.075% Bisulfite (CD:Arg 1.0:1.2) | 0.25 | 2.4 | 1.2 | 8.3 |

TABLE N

Total degradation products: Peak area (%)

|  |  |  | T = 1 week 2-8° C. |  | T = 1 week 25° C. |
|---|---|---|---|---|---|
|  |  | t = 0 | Air | N2 | Air |
| 1 | 0.4% ascorbic + 0.2% cysteine (CD:Arg 1.0:1.5) | 0.1 | 2.5 | 1.1 | 7.2 |
| 2 | 0.075% Bisulfite (CD:Arg 1.0:1.5) | 0.2 | 2.6 | 2.1 | 7.7 |
| 3 | 0.075% Bisulfite (CD:Arg 1.0:1.2) | 0.25 | 3.1 | 2.1 | 9.8 |

The results as presented in Tables M and N indicate that formulations containing more arginine are more stable when exposed to air at 25° C. (formulations 2 vs. 3). Further, formulations containing Na-bisulfite are less stable than the formulation containing ascorbic acid and L-cysteine (formulations 2 vs. 1, respectively) when stored under nitrogen (anaerobic conditions). $N_2$ provided significant protection from degradation and degradant formation. Formulations exposed to air are more stable when kept refrigerated, as compared to room (ambient) temperature.

Example 10: Effect of Various Antioxidants on the Stability of Formulations Containing 4% Carbidopa at 40° C.

Liquid formulations with carbidopa and arginine (Table O) were prepared as described above. The effect various antioxidants on the stability of formulations containing 4% CD at 40° C. was evaluated using HPLC analysis. The levels of the degradant and total impurities, presented in tables P and Q respectively, indicate the level of stability of carbidopa formulations.

TABLE O

|  | 1 | 2 | 3 | 4 |
|---|---|---|---|---|
| Carbidopa | 4.0 | 4.0 | 4.0 | 4.0 |
| L-Arginine | 3.4 | 3.7 | 4.6 | 4.6 |
| N-MP | 3.5 | 0 | 0 | 0 |
| Ascorbic acid | 0 | 0 | 0.4 | 0.5 |
| Cysteine | 0 | 0 | 0.2 | 0.1 |
| Na bisulfite | 0.1 | 0.075 | 0 | 0 |
| Total solutes | 12.9 | 9.2 | 9.2 | 9.2 |
| Water | 87.1 | 90.8 | 90.8 | 90.8 |
| L-Arg (mM) | 195 | 212 | 265 | 265 |
| CD (mM) | 177 | 177 | 177 | 177 |
| Ratio L-Arg/CD | 1.1 | 1.2 | 1.5 | 1.5 |
| pH measured | 8.76 | 8.96 | 9.13 | 9.12 |

TABLE P

Degradant

|  | t = 0 | t = 2d/40° C. | t = 5d/40° C. |
|---|---|---|---|
| 1 4% CD – 3.4% L-Arg + 3.5% N-MP 0.1% sodium bisulfite | 0.27 ± 0.01 | 1.52 ± 0.56 | 2.60 ± 0.67 |
| 2 4% CD – 3.7% L-Arg 0.075% sodium bisulfite | 0.30 ± 0.01 | 1.41 ± 0.54 | 2.95 ± 0.60 |
| 3 4% CD – 4.62% L-Arg 0.4% ascorbic + 0.2% L-cysteine | 0.06 ± 0.01 | 0.38 ± 0.14 | 1.26 ± 0.45 |
| 4 4% CD – 4.62% L-Arg 0.5% ascorbic + 0.1% L-cysteine | 0.11 ± 0.01 | 0.50 ± 0.23 | 1.97 ± 0.52 |

TABLE Q

Total impurities

|  | t = 0 | t = 2d/40° C. | t = 5d/40° C. |
|---|---|---|---|
| 1 4% CD – 3.4% L-Arg + 3.5% N-MP 0.1% sodium bisulfite | 0.61 | 2.00 ± 0.54 | 3.19 ± 0.65 |
| 2 4% CD – 3.7% L-Arg 0.075% sodium bisulfite | 0.60 | 1.86 ± 0.56 | 3.61 ± 0.60 |
| 3 4% CD – 4.62% L-Arg 0.4% ascorbic + 0.2% L-cysteine | 0.29 | 0.92 ± 0.16 | 2.15 ± 0.59 |
| 4 4% CD – 4.62% L-Arg 0.5% ascorbic + 0.1% L-cysteine | 0.34 | 1.17 ± 0.28 | 2.82 ± 0.61 |

The results presented in Tables P and Q suggest that formulations containing Na-bisulfite are less stable than the formulations containing ascorbic acid and L-cysteine (formulations 1 & 2 vs. 3 & 4), both during preparation and when stored at 40° C. Furthermore, there was a cysteine dose-response, i.e., the higher the concentration of L-cysteine, the less degradant was formed. No dose response was observed with Na-bisulfite, suggesting that the maximum possible protection may be attained with 0.075% Na-bisulfite.

Example 11: Effect of Ascorbic Acid Combined with Various Antioxidants on the Stability of Formulations Containing 4% Carbidopa Liquid formulations with carbidopa and ascorbic acid with or without additional antioxidants were prepared as described above. The combination effect between ascorbic acid and various antioxidants on the stability of formulations containing 4% CD at 25° C. was evaluated using HPLC analysis. The levels of the degradant and total impurities presented in tables R and S respectively, point toward the level of stability of carbidopa formulations.

TABLE R

| 4% CD | t = 0 | t = 3d at 25° C./$N_2$ | t = 2d at 25° C./$O_2$ |
|---|---|---|---|
| Degradant | | | |
| Without antioxidants | 0.24 | 1.29 | 3.27 |
| 0.5% Asc | 0.54 | 3.17 | 5.09 |
| 0.5% Asc + 0.2% bisulfite | 0.16 | 0.76 | 2.98 |
| 0.5% Asc + 0.2% cysteine | 0.09 | 0.27 | 2.67 |
| 0.5% Asc + 0.2% NAC | 0.14 | 0.83 | 3.64 |
| 0.75% bisulfite (CONTROL) | 0.39 | 1.23 | 2.98 |

TABLE S

| 4% CD | t = 0 | t = 3d at 25° C./$N_2$ | t = 2d at 25° C./$O_2$ |
|---|---|---|---|
| Total impurities | | | |
| Without antioxidants | 1.04 | 1.88 | 4.01 |
| 0.5% Asc | 1.07 | 3.96 | 6.40 |
| 0.5% Asc + 0.2% bisulfite | 0.70 | 1.29 | 3.64 |
| 0.5% Asc + 0.2% cysteine | 0.67 | 0.74 | 3.43 |
| 0.5% Asc + 0.2% NAC | 0.72 | 1.36 | 4.49 |
| 0.75% bisulfite (CONTROL) | 1.13 | 1.71 | 3.58 |

Results presented in Tables R and S show that ascorbic acid, 0.5%, was insufficient for the prevention of degradant formation in a formulation containing carbidopa. Furthermore, ascorbic acid requires another antioxidant in order to exert its maximum antioxidant activity, for example ascorbic acid, 0.5%, and L-cysteine, NAC, or Na-bisulfite inhibited carbidopa degradation in a synergistic manner. Formulations containing ascorbic acid and L-cysteine had the lowest amount of degradant after 3 days at 25° C.

The effect of Na-bisulfite on carbidopa degradation was similar to that obtained with no antioxidants at all.

Example 12: Effect of Antioxidants on the Stability of 4% CD Formulations Stored at 25° C.

Liquid formulations with carbidopa and arginine (Table T) were prepared as described above. The effect of various antioxidants on the stability of formulations containing 4% carbidopa at 25° C. was evaluated using HPLC analysis. The levels of the degradant and total impurities presented in Table W, point toward the level of stability of carbidopa formulations.

TABLE T

| | 1 | 2 | 3 | 4 | 5 | 6 | 7 |
|---|---|---|---|---|---|---|---|
| Carbidopa | 4.0 | 4.0 | 4.0 | 4.0 | 4.0 | 4.0 | 4.0 |
| L-Arginine | 4.6 | 4.6 | 4.6 | 4.6 | 4.6 | 4.6 | 4.6 |
| Ascorbic acid | 0.2 | 0.5 | 0.2 | 0.0 | 0.0 | 0.0 | 0.2 |
| Cysteine | 0.0 | 0.2 | 0.2 | 0.2 | 0.2 | 0.0 | 0.0 |
| Na bisulfite | 0.0 | 0.0 | 0.0 | 0.0 | 0.1 | 0.1 | 0.1 |

TABLE W

| | Degradant | | TOTAL Impurities | |
|---|---|---|---|---|
| | t = 0 | t = 1 wk | t = 0 | t = 1 wk |
| 1 0.2% ascorbic acid | 0.48 | 1.43 | 1.20 | 2.11 |
| 2 0.5% ascorbic acid/ 0.2% cysteine | 0.12 | 0.17 | 0.81 | 0.72 |
| 3 0.2% ascorbic acid/ 0.2% cysteine | 0.12 | 0.21 | 0.85 | 0.94 |
| 5 0.2% cysteine | 0.26 | 0.53 | 1.02 | 1.00 |
| 5 0.2% cysteine/ 0.1% bisulfite | 0.71 | 1.01 | 1.62 | 1.66 |
| 6 0.1% bisulfite | 0.33 | 0.84 | 1.16 | 1.45 |
| 7 0.2% ascorbic acid/ 0.1% bisulfite | 0.26 | 0.70 | 0.99 | 1.49 |

Results presented in Table W suggest that ascorbic acid, bisulfite, or cysteine, each used alone, did not inhibit degradant formation. Combinations between bisulfite and cysteine or ascorbic acid did not inhibit degradant formation. There was a synergistic inhibitory effect on degradant formation between ascorbic acid and cysteine, but no such synergism between cysteine and bisulfite was observed. Such synergistic effects can be seen between ascorbic acid and bisulfite (with higher ascorbic acid concentrations). These results further suggest that formulations containing the unique combination of ascorbic acid and cysteine may provide the best means for the inhibition of degradant formation.

Ascorbic acid, at 0.2%, was not sufficient for the prevention of degradant formation. With 0.2% cysteine, 0.5% ascorbic acid was more effective than 0.2% in reducing the total amount of impurities and degradant formation, suggesting that at least 0.5% ascorbic acid with 0.2% cysteine is desirable.

Example 13: Determination of the Level of Hydrazine in Carbidopa Formulations

The determination of hydrazine was carried out by derivatization using Aceton-d6. The hydrazine derivative was analyzed by gas chromatography mass spectrometry (GC/MS). The specific mass of hydrazine derivative was measured in the selected ion monitoring mode (SIM-mode) according to Solvias standard operating procedures (SOP's).

Liquid formulations with carbidopa, levodopa, and arginine (Table X) were prepared as described above. The levels of hydrazine in the referenced formulations were measured (Table Y).

TABLE X

| Formulation Composition (%) | | | | | | | | | | |
|---|---|---|---|---|---|---|---|---|---|---|
| | Formulation # | | | | | | | | | |
| | 1 | 2 | 3 | 4 | 5 | 6 | 7 | 8 | 9 | 10 |
| Carbidopa | 4 | 4 | 1.4 | 1.4 | 1.4 | 1.4 | 0.75 | 1.4 | 0.75 | 0.75 |
| Levodopa | — | — | 6 | 6 | 6 | 6 | 6 | 6 | 6 | 6 |
| Arginine | 4.6 | 4.6 | 14.8 | 15.5 | 15.5 | 15.5 | 15.2 | 15.5 | 15.2 | 15.2 |
| Ascorbic acid | 0.4 | 0.5 | 0.75 | 0.5 | 0.5 | 0.5 | 0.5 | 0.5 | 0.5 | 0.5 |
| L-Cysteine | 0.2 | 0.1 | — | 0.4 | 0.4 | — | — | 0.4 | 0.4 | 0.4 |
| NAC | — | — | — | — | — | 0.5 | 0.5 | — | — | — |
| Tween 80 | — | — | — | — | — | — | — | — | — | 0.3 |
| Sodium Ascorbate | — | — | — | — | — | — | — | — | — | — |
| | Formulation # | | | | | | | | | |
| | 11 | 12 | 13 | 14 | 15 | 16* | 17** | 18 | 19 | 20 |
| Carbidopa | 1.4 | 0.75 | 1.4 | 1.4 | 3 | 1.5 | 1.5 | 1.4 | 3 | 1.3 |
| Levodopa | 6 | 6 | 6 | 6 | 12 | 6 | 6 | 6 | 12 | 12 |
| Arginine | 15.5 | 15.2 | 15.5 | 15.5 | 32.3 | 15.5 | 15.5 | 15.5 | 32.3 | 29 |
| Ascorbic acid | 0.5 | 0.5 | 0.5 | 0.5 | — | 0.5 | 0.5 | 0.5 | | |
| L-Cysteine | 0.4 | — | — | 0.4 | 0.3 | 0.4 | 0.4 | 0.4 | | |
| NAC | — | 0.5 | 0.5 | — | — | — | — | — | 0.3 | 0.3 |
| Tween 80 | 0.3 | 0.3 | 0.3 | 0.3 | — | 0.3 | 0.3 | 0.3 | | |
| Sodium Ascorbate | — | — | — | — | 1.2 | — | — | — | 1.2 | 1.2 |

*Sealed with N2
**Sealed with O$_2$

TABLE Y

| Storage in vials | Time and temp prior to analysis (in-use stability) | Hydrazine (ppm) | | | | | | | | | |
|---|---|---|---|---|---|---|---|---|---|---|---|
| | | 1 | 2 | 3 | 4 | 5 | 6 | 7 | 8 | 9 | 10 |
| T = 0 at −20° C. | | | | | | | | | | | |
| 1 month at −20° C. | 24 h  25° C. | | 0.82 | 0.77 | 0.39 | | | | | | |
| | 48 h | | 0.73 | 0.71 | 0.43 | | | | | | |
| | 24 h  37° C. | | 0.76 | 0.84 | 0.41 | | | | | | |
| | 48 h | | 0.87 | 0.93 | 0.59 | | | | | | |
| 3 months at −20° C. | | | | | | | | | <0.1 | <0.1 | |
| 6 months at −20° C. | 3 free-thaw cycles (25° C.) | | | | | 0.1 | 0.1 | | | | 0.1 |
| 9 months at −20° C. | | | | | | | | | | | 0.1 |
| 1 year at −20° C. | 24 h  25° C. | | | | <0.1 | | | | | | |
| | 37° C. | | | | <0.1 | | | | | | |
| | | | | | | | | | | | 0.1 |
| 24 hr | 37° C. | | | | | | | | | | |
| 7 days at 25° C. | 24 h  37° C. | | | | | <0.1 | <0.1 | <0.1 | | | |
| 1 month 25° C. | | | | | | | 0.1 | <0.1 | | | |

| Storage in vials | Time and temp prior to analysis (in-use stability) | Hydrazine (ppm) | | | | | | | | | |
|---|---|---|---|---|---|---|---|---|---|---|---|
| | | 11 | 12 | 13 | 14 | 15 | 16 | 17 | 18 | 19 | 20 |
| T = 0 at −20° C. | | <0.1 | <0.1 | <0.1 | | | | | | | |
| 1 month at −20° C. | 24 h  25° C. | | | | | | | | | | |
| | 48 h | | | | | | | | | | |
| | 24 h  37° C. | | | | | | | | | | |
| | 48 h | | | | | | | | | | |
| 3 months at −20° C. | | | | | | | 0.1 | 0.1 | | | |
| 6 months at −20° C. | 3 free-thaw cycles (25° C.) | | | | | | | | | | |
| | | 0.1 | <0.1 | 0.1 | | | | | 0.1 | | |

TABLE Y-continued

| | | | | | | | | |
|---|---|---|---|---|---|---|---|---|
| 9 months at −20° C. | | | 0.1 | | 0.1 | | | |
| 1 year at −20° C. | 24 h | 25° C. 37° C. | | | | | | |
| | | | 0.1 | <0.1 | 0.1 | 0.1 | | |
| 24 hr | | 37° C. | | <0.1 | 0.1 | | <0.1 | |
| 7 days at 25° C. | 24 h | 37° C. | | | | | | |
| 1 month 25° C. | | | | | 0.1 | | 0.3 | 0.1 |

The results presented in Table Y clearly show that the levels of hydrazine is at least 2 fold lower in levodopa formulations versus formulations without levodopa. Furthermore, formulations comprising L-cysteine or NAC show at least 4-fold lower levels of hydrazine compared to formulations without L-cysteine or NAC.

Example 14: Carbidopa/Levodopa Formulations

Based on the discoveries of combinations that have reduced degradant and hydrazine formation, we have developed new CD/LD formulations. These formulations are shown in Tables Z and AA below.

TABLE Z

| DS (%) | LD | CD | Arginine | Ascorbic Acid | L-Cysteine | NAC | Tween-80 | pH |
|---|---|---|---|---|---|---|---|---|
| 1 | 6 | 1.4 | 15.5 | 0.5 | 0.4 | — | 0.3 | 9.4-9.6 |
| 2 | 6 | 1.4 | 15.5 | 0.5 | — | 0.5 | 0.3 | 9.4-9.6 |
| 3 | 6 | 0.75 | 15.2 | 0.5 | 0.4 | — | 0.3 | 9.4-9.6 |
| 4 | 6 | 0.75 | 15.2 | 0.5 | — | 0.5 | 0.3 | 9.4-9.6 |
| Margins | 6 | 0.6-1.4 | 15-16 | 0.5 | 0.4 | 0.5 | 0.3 | 9.4-9.6 |

TABLE AA

| DS (%) | LD | CD | Arginine | Meglumine | Sodium Ascorbate | L-Cysteine | NAC | Cysteine-HCl | Tween-80 | pH |
|---|---|---|---|---|---|---|---|---|---|---|
| 1 | 12 | 3 | 32 | — | 1.2 | 0.3 | — | — | — | 9.6-9.8 |
| 2 | 13.2 | 3.3 | 36 | — | 1.3 | 0.3 | — | — | — | 9.6-9.8 |
| 3 | 13.2 | 3.3 | — | 36 | 1.3 | 0.3 | — | — | — | 9.6-9.8 |
| 4 | 12 | 3 | — | 32 | 1.2 | — | 0.3 | — | — | 9.6-9.8 |
| 5 | 12 | 3 | 32 | — | 1.2 | — | 0.3 | — | — | 9.6-9.8 |
| | 12-15 | 1.2-4 | 32-42 | 32-42 | 1.0-1.3 | | 0.1-0.5* | | ≤2** | 9.6-9.8 |

\* Can replace L-cysteine.
\*\*Optionally added to stabilize the formulation.

Additional formulations that may be used in the context of those disclosed herein are provided in Table BB below. The formulations may include additional components (e.g., any of those described herein). Tables CC and DD described further formulations that can be used in the context of those described herein.

TABLE BB

| Levodopa Conc. (%) | Carbidopa Conc. (%) | Amino Acid | | Other | |
|---|---|---|---|---|---|
| | | Name | Conc. (%) | Name | Conc. (%) |
| 3 | 0 | Lys | 5.6 | | |
| 2.5 | 0 | Lys | 4.6 | | |
| 1.25 | 0 | His | 2.5 | | |
| 9.5 | 0 | Arg | 15.9 | | |
| 4.8 | 1.4 | Arg | 11.0 | | |
| 4.8 | 1.4 | Arg | 12.1 | | |
| 4.8 | 1.4 | Arg | 12.7 | | |
| 5.4 | 1.5 | Arg | 13.5 | | |
| 5.4 | 1.5 | Arg | 14.8 | | |
| 6 | 1.5 | Arg | 14.8 | | |
| 6 | 1.5 | Arg | 16.0 | | |
| 7 | 2 | Arg | 17.8 | | |
| 7 | 1.5 | Arg | 14.1 | Dextrose | 5.0 |
| 8 | 1.5 | Arg | 15.7 | Dextrose | 5.0 |
| 10 | 1.5 | Arg | 19.2 | Dextrose | 5.0 |
| 6 | 1.5 | Arg | 9.3 | NaOH | 4.6 |
| 5 | 0 | | | Meglumine | 10.8 |
| 8 | 1.5 | Arg | 15.7 | Meglumine | 3.2 |
| 8 | 1.5 | Arg | 12.2 | Meglumine | 7.9 |
| 10 | 1.5 | Arg | 19.2 | Meglumine | 4.0 |
| 10 | 1.5 | Arg | 14.6 | Meglumine | 9.9 |
| 7 | 1.5 | Arg | 14.1 | Meglumine | 2.8 |
| 7 | 1.5 | Arg | 10.7 | Meglumine | 6.9 |
| 6 | 1.5 | Arg | 13.5 | Na-Asc | 1 |
| 6 | 1.5 | Arg | 14.2 | Na-Asc | 1 |
| 6 | 1.5 | Arg | 14.8 | Na-Asc | 1 |
| 6 | 1.5 | Arg | 16.0 | Na-Asc | 1 |
| 4.8 | 1.4 | Arg | 11.0 | Na-Asc | 1 |
| 4.8 | 1.4 | Arg | 11.6 | Na-Asc | 1 |
| 4.8 | 1.4 | Arg | 12.1 | Na-Asc | 1 |
| 4.8 | 1.4 | Arg | 12.7 | Na-Asc | 1 |
| 6 | 1.5 | Arg | 14.8 | Asc | 1 |
| 6 | 1.5 | Arg | 15.8 | Na-Asc | 1 |
| 6 | 1.5 | Arg | 15.8 | Asc | 1 |

TABLE BB-continued

| Levodopa Conc. (%) | Carbidopa Conc. (%) | Amino Acid Name | Conc. (%) | Other Name | Conc. (%) |
|---|---|---|---|---|---|
| 6 | 1.5 | Arg | 16.8 | Na-Asc | 1 |
| 6 | 1.5 | Arg | 16.8 | Asc | 1 |
| 5.4 | 1.5 | Arg | 12.3 | Na-Asc | 1 |
| 5.4 | 1.5 | Arg | 12.3 | Asc | 1 |
| 5.4 | 1.5 | Arg | 13.5 | Na-Asc | 1 |
| 5.4 | 1.5 | Arg | 13.5 | Asc | 1 |
| 5.4 | 1.5 | Arg | 14.8 | Na-Asc | 1 |
| 5.4 | 1.5 | Arg | 14.8 | Asc | 1 |
| 6 | 1.5 | Arg | 16.0 | Asc | 1 |
| 7 | 2 | Arg | 17.8 | Asc | 1 |
| 7 | 2 | Arg | 17.8 | Na-Asc | 1 |
| 12 | 3 | Arg | 24.4 | | |
| 12 | 3 | Arg | 29.6 | | |
| 12 | 3 | Arg | 32.1 | | |
| 7 | 0 | Arg | | | |
| 7 | 0.5 | Arg | | | |
| 7 | 1 | Arg | | | |
| 7 | 1.5 | Arg | | | |
| 7 | 2 | Arg | | | |
| 6 | 0 | Arg | 13.5 | | |
| 6 | 0.5 | Arg | 14.2 | | |
| 6 | 1 | Arg | 14.8 | | |
| 6 | 2 | Arg | 16.5 | | |
| 0 | 2 | | | | |

TABLE CC

| Property | | 1 | 2 | 3 |
|---|---|---|---|---|
| API Concentration | | 2 & 4% | 4% | 0.6-20% |
| CD:Arginine ratio | | 1:1.1-1.2 | 1:1.5 | 1:≥1 |
| Exipients concentration | NMP | 3.5% | 0 | 0-15% |
| | Na-bisulfite | 0.1% | 0 | 0-0.2% |
| | Ascorbic Acid | 0 | 0.75% | 0-2% or more |
| | L-Cysteine or NAC | 0 | 0.1% | 0-0.5% or more |
| | Other anti-oxidants | — | — | 0-2% |
| Osmolality | | 650-750 | 300-400 | 200-1800 for SC No limits for ID |
| pH | | 8.2-8.6 | 8.6-9.1 | 8-9.8 |
| Stability | 25° C. | 48-72 hrs | ≥21 d | 2 wks-≥2yrs |
| | 4° C. | Not stable | ≥21 d | 2 wks-≥2yrs |
| | −20° C. | ≥1 year | ≥21 d | 2 wks-≥2yrs |
| SC Infusion/24 hrs | | 2 ml | 2 ml | 0.1-20 ml |

TABLE DD

| Property | | 4 | 5 | 6 |
|---|---|---|---|---|
| API Concentration | CD | 0 or 1 or 2% | 1-2% | 0-4% up to 6% |
| | LD | 3-7% | 5-7% | 2.5-12% up to 14% |
| Ratios | LD to CD Ratio | 6:1-6:3 or LD alone | 3.5-4:1 | 1:1-10:0.5 |
| | CD:Arginine Ratio | 1:1.2 | 1:9-14 | 1: ≥35 |
| | LD:Arginine Ratio | 1:1.8-2.2 | 1:2-3.5 | 1: ≥3.6 |
| | API: Arginine Ratio | [1:1.2 CD:Arg + 1:2 LD:Arg] + 12.5% Arg | 1:2.3-2.5 | 1: ≥1.8 |
| Exipients | NMP | 0 | 0 | 0 |
| | Na-bisulfite | 0.075-0.15% | 0 | 0-0.2% |

TABLE DD-continued

| Property | | 4 | 5 | 6 |
|---|---|---|---|---|
| | Ascorbic Acid | 0 | 0.75 | 0-2% or more |
| | Other anti-oxidants | — | — | 0-2% |
| Osmolality | 9/1% LD/CD | 1300-1500 | | 200-1800 for SC |
| | 7/2% LD/CD | 950-1150 | 1200-1300 | No limits for ID |
| | 6/1.5% LD/CD | 800-850 | 940-980 | |
| | 5/1.25% LD/CD | NT | 790-830 | |
| pH | | 8.5-9.5 | 9.2-9.6 | 9.1-9.8 |
| Stability | 25° C. | ≥2 days | ≥2 days | ≥2 days |
| | 4° C. | <2 days | ≥2 days | ≥2 days |
| | −20° C. | ≥2 days | ≥2 days | ≥2 days |
| SC Infusion/24 hrs | | 2 ml | 2-6 ml | 0.1-10 ml/site |
| Intraduodenal/24 hrs | | — | — | 4-24 ml |
| Intrathecal | | — | — | 1-1000 µl/day |

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

INCORPORATION BY REFERENCE

The entire contents of all patents, published patent applications, websites, and other references cited herein are hereby expressly incorporated herein in their entireties by reference.

What is claimed is:

1. A method for treating Parkinson's disease in a patient, the method comprising administering to the patient a pharmaceutically acceptable liquid formulation comprising:
   about 6% by weight levodopa;
   about 0.75% by weight carbidopa;
   about 10% to about 20% by weight arginine;
   about 0.5% by weight of L-cysteine or NAC; and
   about 0.5% by weight ascorbic acid, or a salt thereof,
   wherein the formulation, after 24 hours at 25° C., has less than about 0.1 µg/ml hydrazine, as determined by GCMS, and
   wherein the administering is in an amount of the formulation effective to treat Parkinson's disease in the patient.

2. The method of claim 1, wherein the pharmaceutically acceptable liquid formulation has less than about 1% by weight 3,4-dihydroxyphenyl-2-methylpropionic acid (degradant), relative to the amount of carbidopa, as determined by HPLC.

3. The method of claim 1, wherein the pharmaceutically acceptable liquid formulation, after 30 days at 25° C., has less than about 0.1 µg/ml hydrazine, as determined by GCMS.

4. The method of claim 1, wherein the pharmaceutically acceptable liquid formulation further comprises a surfactant.

5. The method of claim 1, wherein the administering is substantially continuous.

6. The method of claim 1, wherein the patient is a human.

7. The method of claim 1, wherein the administering is at a rate of about 0.16 ml/hour/site to about 0.24 ml/hour/site.

8. The method of claim 1, wherein the administering is at a rate of about 0.01 ml/hour/site to about 0.4 ml/hour/site.

9. The method of claim 1, wherein the administering is intraduodenal and at a rate of about 1.0 ml/hour during the daytime and at a rate of 0 ml/hour to about 0.5 ml/hour at night.

10. The method of claim 1, wherein the pharmaceutically acceptable liquid formulation is administered subcutaneously.

\* \* \* \* \*